United States Patent
Alpaslan et al.

(10) Patent No.: US 11,931,433 B2
(45) Date of Patent: Mar. 19, 2024

(54) DRY SHAMPOO COMPOSITION

(71) Applicant: Church & Dwight Co., Inc., Princeton, NJ (US)

(72) Inventors: Seyfi Alpaslan, Folkestone (GB); Shirish Desale, Ashford (GB)

(73) Assignee: Church & Dwight Co., Inc., Princeton, NJ (US)

( * ) Notice: Subject to any disclaimer, the term of this patent is extended or adjusted under 35 U.S.C. 154(b) by 174 days.

(21) Appl. No.: 17/185,676

(22) Filed: Feb. 25, 2021

(65) Prior Publication Data

US 2021/0267855 A1 Sep. 2, 2021

Related U.S. Application Data

(60) Provisional application No. 62/983,261, filed on Feb. 28, 2020.

(51) Int. Cl.
| | |
|---|---|
| A61Q 5/00 | (2006.01) |
| A61K 8/04 | (2006.01) |
| A61K 8/31 | (2006.01) |
| A61K 8/34 | (2006.01) |
| A61K 8/73 | (2006.01) |
| A61Q 5/02 | (2006.01) |
| A61Q 5/06 | (2006.01) |

(52) U.S. Cl.
CPC ............... *A61K 8/046* (2013.01); *A61K 8/31* (2013.01); *A61K 8/34* (2013.01); *A61K 8/732* (2013.01); *A61Q 5/02* (2013.01); *A61Q 5/065* (2013.01)

(58) Field of Classification Search
CPC . A61K 8/046; A61K 8/31; A61K 8/34; A61K 8/732; A61K 8/416; A61K 2800/31; A61Q 5/02; A61Q 5/065

USPC ........................................................ 510/120
See application file for complete search history.

(56) References Cited

U.S. PATENT DOCUMENTS

| | | | |
|---|---|---|---|
| 6,248,338 B1 | 6/2001 | Muller et al. | |
| 7,481,996 B2 | 1/2009 | Ishii et al. | |
| 9,161,898 B2 | 10/2015 | Schweinsberg | |
| 9,327,144 B2 | 5/2016 | Cohen et al. | |
| 9,757,321 B2 | 9/2017 | Cajan et al. | |
| 10,010,489 B2 | 7/2018 | Argembeaux et al. | |
| 2016/0106634 A1* | 4/2016 | Gawtrey | A61K 8/19 |
| | | | 424/47 |
| 2017/0014314 A1 | 1/2017 | McElligott et al. | |
| 2017/0202755 A1 | 7/2017 | Malle et al. | |

(Continued)

FOREIGN PATENT DOCUMENTS

| | | |
|---|---|---|
| DE | 2943521 | 5/1981 |
| DE | 102017220775 | 6/2018 |

(Continued)

OTHER PUBLICATIONS

Batiste Dry shampoo Dark and Brown 200Ml (Nov. 23, 2015).*

(Continued)

*Primary Examiner* — Eisa B Elhilo
(74) *Attorney, Agent, or Firm* — Church & Dwight Co., Inc.

(57) ABSTRACT

The present disclosure provides dry shampoo compositions effective for cleaning hair and also coloring hair. The dry shampoo compositions can include a starch component mixed with a colorant, a color adhesion promoter, a solvent, and optional further ingredients, such as propellants and fragrances.

12 Claims, 8 Drawing Sheets

(56) References Cited

U.S. PATENT DOCUMENTS

| | | | |
|---|---|---|---|
| 2017/0216181 A1* | 8/2017 | Aubert | A61K 8/29 |
| 2017/0312212 A1 | 11/2017 | Aubert et al. | |
| 2017/0319448 A1* | 11/2017 | Aubert | A61K 8/25 |
| 2018/0104171 A1 | 4/2018 | Constantine et al. | |
| 2018/0153782 A1* | 6/2018 | Desale | A61Q 5/02 |
| 2018/0168986 A1 | 6/2018 | Knappe et al. | |
| 2018/0289601 A1 | 10/2018 | Eppler et al. | |
| 2019/0008751 A1* | 1/2019 | Mustafa | A61Q 5/02 |
| 2019/0029936 A1 | 1/2019 | Bradt | |
| 2019/0070092 A1* | 3/2019 | Knappe | A61K 8/8141 |
| 2019/0240121 A1 | 8/2019 | Torres et al. | |
| 2019/0269587 A1 | 9/2019 | Burgo | |

FOREIGN PATENT DOCUMENTS

| | | | |
|---|---|---|---|
| EP | 2930126 | 10/2015 | |
| EP | 2846759 | 11/2017 | |
| EP | 3468522 | 4/2019 | |
| EP | 3500233 | 6/2019 | |
| FR | 2904542 | 6/2011 | |
| FR | 3027799 | 12/2017 | |
| FR | 3071413 | 3/2019 | |
| FR | 3017288 | 6/2019 | |
| FR | 3075637 | 6/2019 | |
| GB | 2520436 | 5/2016 | |
| GB | 2564217 A * | 1/2019 | A61Q 5/02 |
| GB | 2570560 | 7/2019 | |
| WO | 2017109182 | 6/2017 | |
| WO | WO 2018/106694 A1 * | 6/2018 | A61K 8/81 |
| WO | 2018216242 | 11/2018 | |
| WO | 2019057829 | 3/2019 | |
| WO | 2019083270 | 5/2019 | |
| WO | 2019101379 | 5/2019 | |
| WO | 2019193949 | 10/2019 | |

OTHER PUBLICATIONS

"Batiste Dry Shampoo Dark And Brown 200Ml", (Batiste) Nov. 23, 2015 (Nov. 23, 2015) [Retrived on Apr. 30, 2021) Retrived from Internet <URL:https://www.tesco.com/groceries/en-GB/products/275711193>. GB.

"Comparatively Speaking: Natural- vs. Mineral-based Colorants", (O'Lenick) Mar. 30, 2011 (Mar. 30, 2011) (Retrived on Apr. 30, 2021) Retrived from Internet <URL: https://www.cosmeticsandtoiletries.com/formulating/function/pigment/118610674.html>. US.

"Neossance Hemisqualane", (Humblebee & Me) Mar. 14, 2019 (Mar. 14, 2019) [Retrived on Apr. 30, 2021) Retrived from Internet <URL:https://www.humblebeeandme.com/projecUneossance-hemisqualane/>.US.

* cited by examiner

DRY SHAMPOO COMPOSITION

CROSS-REFERENCE TO RELATED APPLICATIONS

This application claims priority to U.S. Provisional Application No. 62/983,261, filed on Feb. 28, 2020, which application is hereby incorporated by reference in its entirety in this application.

FIELD OF THE INVENTION

The present disclosure relates to compositions for cleaning hair, and more particularly to a dry shampoo composition.

BACKGROUND

This disclosure relates to a natural, dry shampoo and conditioning composition capable of providing longer lasting color effect and imparting superior cleaning and conditioning ability on hair.

Dry hair cleaning compositions for the rapid cleansing of hair are well known. Dry shampoo can be defined as a shampoo in a powder form, used without the addition of water. These known compositions can be used on dry hair in order to freshen up the hair and/or to remove excess oils and other undesirables found on dirty hair. These known compositions are particularly useful when time is short and one cannot wash the hair using wet shampoo.

A common conventional format of dry shampoo is a composition in the form of an aerosol. The aerosol is sprayed into the roots of the hair, massaged in, and combed, a process which can be done very quickly due to the no-rinse formulation. The powders used in dry shampoos are conventionally a starch or starch derivative. Although different starches offer different claimed benefits, they all come to the same end result: quick hair cleaning.

Dry shampoo compositions are well known to the market. See, e.g., PCT/US2017/064721 and U.S. patent application Ser. No. 15/796,884 filed. Oct. 30, 2017 to Henkel AG & Co., which are herein incorporated by reference. Many conventional dry shampoo compositions have the drawback that the powder applied to the hair leaves a white/off-white residue after use, which is a negative experience for the consumer with standard non-colored dry shampoos. As such, a consumer may choose to use a colored dry shampoo product. Colored dry shampoo can be defined as a dry shampoo with colored powder, used without the addition of water. In addition to addressing the problem associated with many conventional non-colored dry shampoos (i.e., the white/off-white residue left in the hair after use), a colored dry shampoo product can be designed for covering gray/white hairs and roots with different color than the main body of hair for different color hairs. However, many conventional colored dry shampoo compositions do not provide a long-lasting color effect because the dry shampoo is coming off the hair more quickly than desired. This problem has been addressed in certain conventional colored dry shampoo compositions by using standard silicone technology used in many conventional hair care products. Many of these products comprise dimethicone (silicone).

There is still a desire and a need to provide a colored dry shampoo composition that is suitable for both cleaning dry hair as well as providing long-lasting color effect.

SUMMARY OF THE INVENTION

In one aspect of the present disclosure, a dry shampoo composition is provided, the dry shampoo composition comprising a starch material, a color adhesion promoter, particularly a long chain alkane, and optionally a propellant. The dry shampoo composition can further comprise a fragrance, for example. In some embodiments, the dry shampoo is substantially free of silicones. In various embodiments, the dry shampoo is substantially free of petroleum-based cationic surfactants.

In various embodiments of the present disclosure, the color adhesion promoter comprises a $C_{13}$-$C_{15}$ alkane. In some embodiments, the color adhesion promoter comprises hemisqualane. The starch material of the dry shampoo composition can comprise a rice starch, for example.

In certain embodiments of the present disclosure, the dry shampoo composition can comprise at least 0.1 weight percent of the starch material, based on the total weight of the dry shampoo composition; at least 0.1 weight percent of the color adhesion promoter, based on the total weight of the dry shampoo composition; and at least 50 weight percent of the propellant, based on the total weight of the dry shampoo composition. In various embodiments, the dry shampoo composition can comprise about 1 to about 12 weight percent of the starch material, based on the total weight of the dry shampoo composition; about 1 to about 12 weight percent of the color adhesion promoter, based on the total weight of the dry shampoo composition; and about 40 to about 95 weight percent of the propellant, based on the total weight of the dry shampoo composition.

In some aspects, the present disclosure also relates to a method of cleansing and conditioning hair. In various embodiments, the method can comprise applying a dry shampoo composition according to the present disclosure to the hair. In particular, the method can comprise spraying or sprinkling the dry shampoo composition on the hair and combing the dry shampoo composition through the hair. The dry shampoo composition can particularly be effective to provide long-lasting color application to the hair. Other aspects and advantages of the disclosure will be apparent from the following.

DETAILED DESCRIPTION OF THE INVENTION

Figure 1:
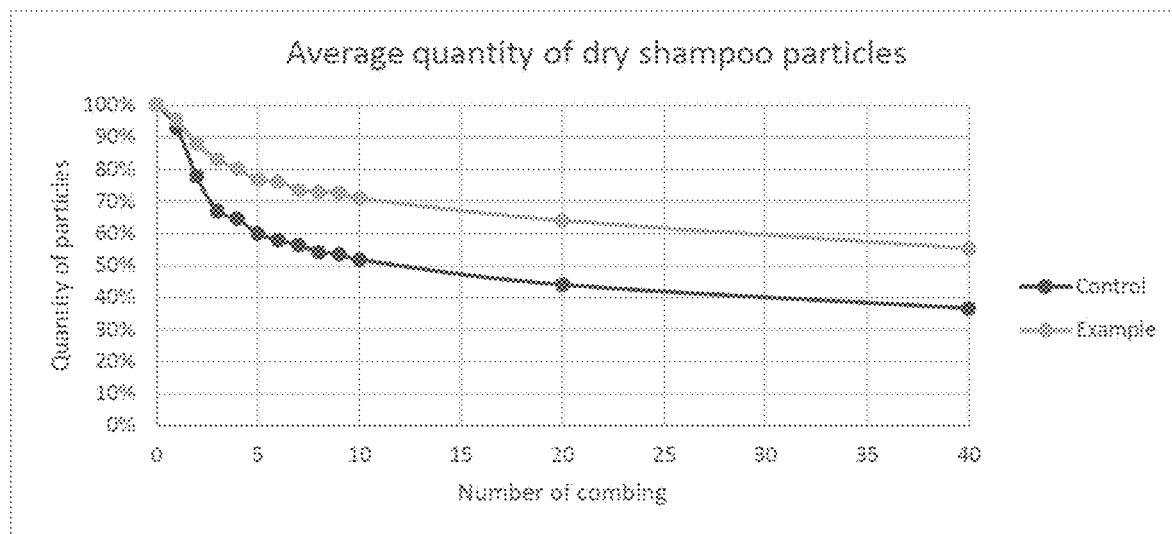
FIG. 1 is a plot of the quantity of shampoo particles remaining in a hair sample by number of combings after treatment of hair with different dry shampoo compositions.

The present disclosure now will be described more fully hereinafter with reference to the accompanying drawings. The disclosure may be embodied in many different forms and should not be construed as limited to the embodiments set forth herein; rather, these embodiments are provided so that this disclosure will satisfy applicable legal requirements. Like numbers refer to like elements throughout. As used in this specification and the claims, the singular forms "a," "an," and "the" include plural references unless the context clearly dictates otherwise.

In one aspect of the present disclosure, a dry shampoo composition is provided which can be topically applied to hair. The term "dry shampoo composition" is understood to relate to a product that is effective to cleanse hair without any necessity for rinsing with water following application. Wet shampoo compositions are understood to be applied to wet hair, lathered, and then rinsed away with added water. A dry shampoo composition, however, can be applied to hair and then optionally be brushed through the hair with the fingers or a utensil (e.g., a comb or brush) to effect the cleansing effect. No rinsing with water is required. A certain amount of liquid components may be included in a dry shampoo composition. Preferably, a dry shampoo composition as disclosed herein comprises less than 5 weight percent, less than 2 weight percent, less than 1 weight percent, or less than 0.1 weight percent of an aqueous component, particularly water, based on the total weight of the dry shampoo composition.

In certain embodiments, the dry shampoo composition can be sprinkled into the hair, or may be sprinkled into a user's hands and then applied to the hair. In various embodiments, the dry shampoo composition can be in the form of an aerosol which can be sprayed onto the hair of a user. The applied composition can be distributed through the hair by massaging into the hair, for example, in order to remove grease, oil and other undesirable elements from soiled hair. Any excess or residual dry shampoo composition powder can be removed from the hair by combing or brushing the hair, for example. In certain embodiments, the dry shampoo composition may leave little or no visible residue in the hair after application.

In various embodiments, the dry shampoo composition can include a plurality of components including, but not limited to, compounds for oil absorption, color adhesion promoters, and emollients. In some embodiments, the dry shampoo composition can further include additional components such as fragrances, color additives, propellants, natural oil (e.g., coconut oil or argan oil), synthetic oil, and the like. A dry shampoo composition of the present disclosure can comprise one or more of each type of component. However, each type of component is not necessarily present in different embodiments of the dry shampoo compositions described herein.

In various embodiments of the present disclosure, the dry shampoo composition can comprise a cleaning agent useful for removing (e.g., absorbing) oil, grease, and other undesirable elements from hair. For example, the dry shampoo composition can comprise at least one starch material that is effective to absorb at least a portion of any oils present on hair. Starch materials useful in the present disclosure include cornstarch, potato starch, tapioca starch, rice starch, wheat starch, cassava starch, and combinations thereof. In certain embodiments, the dry shampoo composition comprises rice starch. A starch material can be modified (e.g., through processes such as esterification, etherification, oxidation, acid hydrolysis, crosslinking, or enzyme conversion) or unmodified.

In some embodiments of the present disclosure, the weight percentage of starch material in the dry shampoo composition, based on the total weight of the dry shampoo composition, can be about 0.1% to about 15%, about 1% to about 12%, about 2% to about 10%, or about 4% to about 8%. In certain embodiments, the weight percentage of starch material in the dry shampoo composition, based on the total weight of the dry shampoo composition, can be at least about 0.1%, at least about 1%, or at least about 4%, preferably with an upper range limit of about 50% by weight.

In various embodiments of the present disclosure, the dry shampoo composition can comprise at least one colorant effective for imparting color to hair. In certain embodiments, the colorant(s) can be in powdered form. Any hair colorant known in the art can be used in the dry shampoo compositions described herein. For example, the colorant can be a blonde colorant, a brunette colorant, a red colorant, a light colorant, a dark colorant, etc.

In some embodiments, the weight percentage of the colorant(s) in the dry shampoo compositions, based on the total weight of the dry shampoo composition, can be about 0.01% to about 5%, about 0.05 to about 2%, or about 0.5 to about 1.5%. In certain embodiments, the weight percentage of the colorant(s) in the dry shampoo composition, based on the total weight of the dry shampoo composition, can be at least about 0.01%, at least about 0.05%, or at least about 1%, preferably with an upper limit of about 5% by weight.

In various embodiments, the dry shampoo composition can comprise a coloring agent formed of a mixture of a starch material and a colorant effective for imparting color to hair. In certain embodiments, the starch material and the colorant, which can also be in powdered form, can be blended and then passed through a pin mill for example, which effectively pulverizes the blend together to provide a uniform mix of color and starch materials. Any hair colorant known in the art can be mixed with the starch material. For example, the colorant can be a blonde colorant, a brunette colorant, a red colorant, a light colorant, a dark colorant, etc. The weight ratio of starch material to colorant within the mixture (i.e., the coloring agent) can be in the range of about 4:1 to about 1:0, or about 9:1 to about 1:0. In various embodiments, the dry weight percentage of the starch material, based on the total weight of the coloring agent (i.e., the mixture of starch material and colorant), is at least about 85%, at least about 90%, at least about 95%, or at least about 98%, preferably with an upper range limit of about 99% by weight.

In some embodiments, the weight percentage of the coloring agent in the dry shampoo compositions, based on the total weight of the dry shampoo composition, can be about 0.01% to about 5%, about 0.05 to about 2%, or about 0.5 to about 1.5%. In certain embodiments, the weight percentage of the coloring agent in the dry shampoo composition, based on the total weight of the dry shampoo composition, can be at least about 0.01%, at least about 0.05%, or at least about 1%, preferably with an upper limit of about 5% by weight.

In various embodiments of the present disclosure, the dry shampoo composition can comprise at least one color adhesion promoter useful for increasing the adhesion of color (e.g., in the form of at least one colorant or a coloring agent as described above) to hair. It was surprisingly found that a long chain alkane can significantly increase the adhesion of a colored dry shampoo composition to treated hair. As used herein, a long chain alkane is at least a $C_{10}$ alkane or at least a $C_{12}$ alkane, preferably up to a $C_{40}$ alkane. For example, in certain embodiments the dry shampoo composition can comprise a color adhesion promoter in the form of a $C_{13}$-$C_{15}$ alkane. In some embodiments, the color adhesion promoter comprises a squalane and/or one or more derivatives thereof, particularly hemisqualane. Without intending to be limited by theory, hemisqualane has a high degree of spread ability, which translates into very good film forming activity evenly coating the hair fiber, thereby resulting in good conditioning performance (slip/combing, static reduction, etc.). Volumizing effects have also been demonstrated with hemisqualane, indicating that there are definite attractions between the hydrophobic regions of the interior of the hair fiber and hemisqualane, causing the migration of it from the surface. It was surprisingly found that these properties enhance adherence of the colorant(s) and/or the starch/colorant mixtures described herein to the hair fibers.

In some embodiments of the present disclosure, the weight percentage of the color adhesion promoter(s) in the dry shampoo composition, based on the total weight of the dry shampoo composition, can be about 0.1% to about 15%, about 1% to about 12%, about 2% to about 10%, or about 0.1% to about 2%. In certain embodiments, the weight percentage of the color adhesion promoter(s) in the dry shampoo composition, based on the total weight of the dry shampoo composition, can be at least about 0.1%, at least about 1%, or at least about 4%, preferably with an upper limit of about 50% by weight.

In some embodiments, the dry shampoo composition can comprise can comprise an emollient useful for moisturizing the hair and thus acting as a conditioning/anti-static agent. Conditioning can separately mean providing a moisturizing effect to the hair and/or providing softness and smoothness to the hair. It is noted that long chain alkanes, as described herein above, can function as a conditioning agent in addition to a color adhesion promoter. However, for the purposes of the present disclosure, long chain alkanes are classified herein as color adhesion promoters. Conditioning agents known in the art include, but are not limited to, silicones (e.g., phenyl trimethicones, dimethicones, cyclomethicones, dimethicone copolyols, amino silicones, etc.), petroleum-based cationic surfactants, distearyldimonium chloride, guar compounds including cationic polymers and guar gum, polycationic compounds designated as polyquaternium 4, 6, 7, 10, or 22, etc. Some of the conditioning agents may provide other functions, such as being a solvent or a flow aid. Preferably, any such conditioning agents are present only in minor concentrations. In various embodiments of the present disclosure, conditioning agents can be expressly excluded from the dry shampoo composition. For example, in certain embodiments, the dry shampoo composition can be substantially free of conditioning agents. As used herein, the term "substantially free of" means that the specified component is present in an amount of less than 0.1 percent by weight, based on the total weight of the composition. In some embodiments, the dry shampoo composition can be entirely free of conditioning agents, meaning that not even trace amounts of conditioning agents are present in the dry shampoo composition beyond the one or more long chain alkanes described herein above, which can also function as a hydrophobic emollient. In certain embodiments, the dry shampoo composition is substantially or entirely free of silicones and/or petroleum-based cationic surfactants. As used herein, the term "petroleum-based cationic surfactants" refers to cationic surfactants that are derived from or which include petroleum, and such surfactants can be expressly excluded from the composition. For example, common cationic surfactants used in the hair care industry (e.g., cetrimonium chloride or behentrimonium chloride) are quaternary ammonium compounds. These compounds are prepared by the alkylation of tertiary amines with a halocarbon/hydrocarbon. As is known in the art, hydrocarbons are (mainly) petroleum-based. In some embodiments, the dry shampoo composition is substantially or entirely free of distearyldimonium chloride, for example.

In some embodiments of the present disclosure, the weight percentage of the emollient(s) in the dry shampoo composition, based on the total weight of the dry shampoo composition, can be about 0.1% to about 15%, about 1% to about 12%, about 2% to about 10%, or about 4% to about 8%. In certain embodiments, the weight percentage of emollient(s) in the dry shampoo composition, based on the total weight of the dry shampoo composition, can be at least about 0.1%, at least about 1%, or at least about 4%, preferably with an upper limit of about 50% by weight.

In various embodiments, the dry shampoo composition can comprise at least one alcohol. The alcohol can be used as a base to dissolve other ingredients (e.g., the at least one color adhesion promoter and/or the at least one conditioning/anti-static agent) in order to provide better adhesion and refreshment of the dry shampoo composition to the treated hair. In various embodiments, the alcohol can be ethyl alcohol.

In some embodiments, the weight percentage of alcohol(s) in the city shampoo composition, based on the total weight of the dry shampoo composition, can be about 0.1% to about 15%, about 1% to about 12%, about 2% to about 10%, or about 4% to about 8%. In certain embodiments, the weight percentage of alcohol(s) in the dry shampoo composition, based on the total weight of the dry shampoo composition, can be at least about 0.1%, at least about 1%, or at least about 4%, preferably with an upper limit of about 20% by weight.

In various embodiments of the present disclosure, the dry shampoo composition can comprise at least one fragrance. In some embodiments, a fragrance can be provided in the form of an essential oil. In certain embodiments, the weight percentage of one or more fragrances in the dry shampoo composition, based on the total weight of the dry shampoo composition, can be about 0.01% to about 3%, about 0.1% to about 2%, or about 0.1% to about 1%. In certain embodiments, the weight percentage of a fragrance in the dry shampoo composition, based on the total weight of the dry shampoo composition, can be at least about 0.01%, at least about 0.1%, or at least about 1%, preferably with an upper limit of about 10% by weight.

In various embodiments, the dry shampoo composition can further include at least one additive useful for adding volume to the treated hair, providing color protection of the treated hair, providing sebum control of the treated hair, providing UV protection of the treated hair, providing frizz control of the treated hair, adding/adjusting texture of the treated hair, and/or enhancing styling of the treated hair. In some embodiments, the at least one additive can be in the form of an extract.

In certain embodiments, the weight percentage of one or more additives in the dry shampoo composition, based on the total weight of the dry shampoo composition, can be about 0.01% to about 3%, about 0.1% to about 2%, or about 0.1% to about 1%. In certain embodiments, the weight percentage of an additive in the dry shampoo composition, based on the total weight of the dry shampoo composition, can be at least about 0.01%, at least about 0.1%, or at least about 1%, preferably with an upper limit of about 10% by weight.

In some embodiments, a dry shampoo composition is provided as an aerosol (e.g., an aerosol dry shampoo composition) and can comprise at least one propellant. Non-limiting examples of propellants include butane, isobutane, propane, liquefied petroleum gas, dimethyl ether, trichlorofluoromethane, dichlorodifluoromethane, dichlorotetrafluorothane, monochlorodifluoromethane, trichlorotrifluoroethane propane, carbon dioxide, nitrous oxide, and combinations thereof. The term "aerosol dry shampoo composition," as used herein, refers to a composition comprising a dry shampoo composition and a propellant. When a dry shampoo composition is provided as an aerosol as compared to a powder, it may advantageously allow for the dry shampoo composition to be applied in a diffusive manner, and may increase the transparency of the dry shampoo composition when compared to powder application. After spraying the aerosol dry shampoo composition onto the hair, the propellant in the dry shampoo composition evaporates and a dry powder remains.

In some embodiments of the present disclosure, the weight percentage of the propellant in the dry shampoo composition, based on the total weight of the dry shampoo composition, can be about 20% to about 98%, about 40% to about 95%, or about 76% to about 90%. In certain embodiments, the weight percentage of carrier material in the dry shampoo composition, based on the total weight of the dry shampoo composition, can be at least about 20%, at least about 40%, at least about 60%, or at least about 80%, preferably with an upper limit of about 98% by weight.

The present dry shampoo composition not only provides a cleansing effect but also provides long-lasting color effect to the treated hair. The dry shampoo compositions described herein can be designed for covering gray/white hairs and/or hair roots with different color than the color of the main body of hair.

A method of preparing a dry shampoo product is also provided herein. In some embodiments, a method of preparing a dry shampoo product can comprise providing a delivery container, adding an oil absorbing agent mixed with at least one colorant to the delivery container, adding a color adhesion promoter to the container (separately or in combination with a fragrance), and adding a propellant to the delivery container. In further embodiments, the method of preparing a dry shampoo product can comprise providing a delivery container, adding a color adhesion promoter to the container (separately or in combination with a fragrance), adding an oil absorbing agent mixed with at least one colorant to the delivery container, and adding a propellant to the delivery container.

In some embodiments, the method of preparing a dry shampoo product can comprise providing a delivery container, adding a dry shampoo composition to the container, and adding a propellant to the delivery container, wherein the dry shampoo composition comprises a color adhesion promoter, optionally a fragrance, an oil absorbing agent, and a colorant.

EXPERIMENTAL

Example 1

A colored dry shampoo composition according to the present disclosure was prepared. The composition is provided in Table 1 (with weight percentage ranges being based on the total weight of the respective dry shampoo composition).

TABLE 1

Composition of the Colored Dry Shampoo Composition of the Present Disclosure

| Phase | Material Function | Ingredient INCL Name | Weight Percentage Range |
|---|---|---|---|
| A | Solvent Base | Ethyl Alcohol | 2.0%-10.0% |
|  | Color Adhesion Promoter | C13-C15 Alkane | 0.1%-10.0% |
|  | Optional Additive Extract | Extract | 0.0%-1.0% |
|  | Fragrance | Parfum | 0.1%-1.0% |
|  | Emollient (conditioning/anti-static agent) | Distearyldimonium Chloride | 0.0%-1.0% |
| B | Oil Absorbent | Oryza Sativa (Rice) Starch | 2.0%-10.0% |
|  | Antistatic Agent | Cetrimonium Chloride | 0.0%-1.0% |
|  | Colorant | Colorant | 0.01%-2% |
| C | Propellant | Butane, Isobutane, Propane | 70.0%-90.0% |

In a mixing vessel, each ingredient in phase A was added and mixed. In a separate mixing vessel, each ingredient in phase B was added and mixed. A product dispensing can was then filled with mixed phase B. The product dispensing can was then filled with mixed phase A. Phase C was added to the dispensing can via a gassing hose.

Product testing showed that the dry shampoo gave hair a cleaner feeling and look after use, and that the dry shampoo worked in a short period of time and was quick/efficient to use. The dry shampoo composition also provided long-lasting color effect, as described in more detail in Example 2 below.

Example 2

The long-lasting color benefit provided by the composition of the present disclosure was evaluated.

A sample dry shampoo composition was prepared according to Example 1 above. A control sample was also prepared for comparison purposes. The control formula was prepared according to the method outlined in Example 1 above, except the control formula does not include any hemisqualanes. The control composition is provided in Table 2 (with weight percentage ranges being based on the total weight of the respective dry shampoo composition).

TABLE 2

Composition of the Colored Dry Shampoo Control Composition

| Phase | Material Function | Ingredient INCL Name | Weight Percentage Range |
|---|---|---|---|
| A | Solvent Base | Ethyl Alcohol | 2.0%-10.0% |
|   | Optional Additive Extract | Extract | 0.0%-1.0% |
|   | Fragrance | Parfum | 0.1%-1.0% |
|   | Emollient (conditioning/anti-static agent) | Distearyldimonium Chloride | 0.0%-1.0% |
| B | Oil Absorbent | Oryza Sativa (Rice) Starch | 2.0%-10.0% |
|   | Antistatic Agent | Cetrimonium Chloride | 0.0%-1.0% |
|   | Colorant | Colorant | 0.01%-2% |
| C | Propellant | Butane, Isobutane, Propane | 70.0%-90.0% |

Figure 2A:
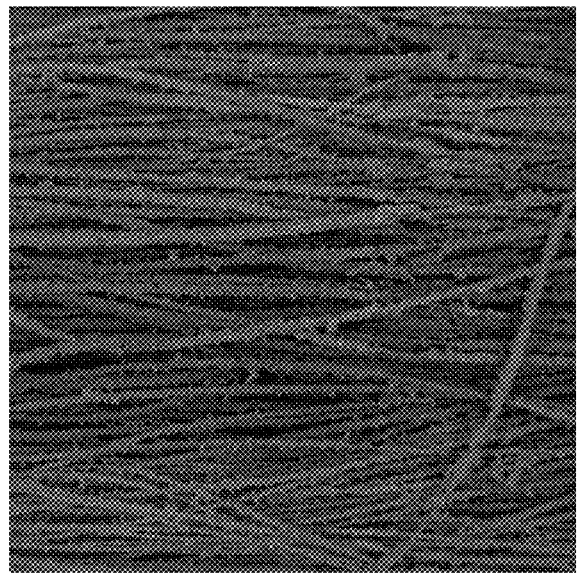
FIGS. 2A-B are high resolution image of natural white hair tresses after different dry shampoo formulations have been applied thereto.
Figure 2B:

After the Example 1 and control formulas were prepared, instrumental deposition analysis was used to analyze the long-lasting benefit of the two formulas. First, high resolution images of natural white hair tresses were captured. Next, each of the Example 1 formula and the control formula were applied to separate white hair tress samples. High resolution images of the treated hair tresses were captured after application of the dry shampoo formulas. FIG. 2(a) is a high resolution image of natural white hair tresses after the control formula has been applied thereto. FIG. 2(b) is a high resolution image of natural white hair tresses after the Example 1 formula has been applied thereto.

Figure 3:
FIG. 3 is a series of high resolution images of a hair tress treated with a colored dry shampoo control formulation after several combings of the treated tress.
Figure 4:
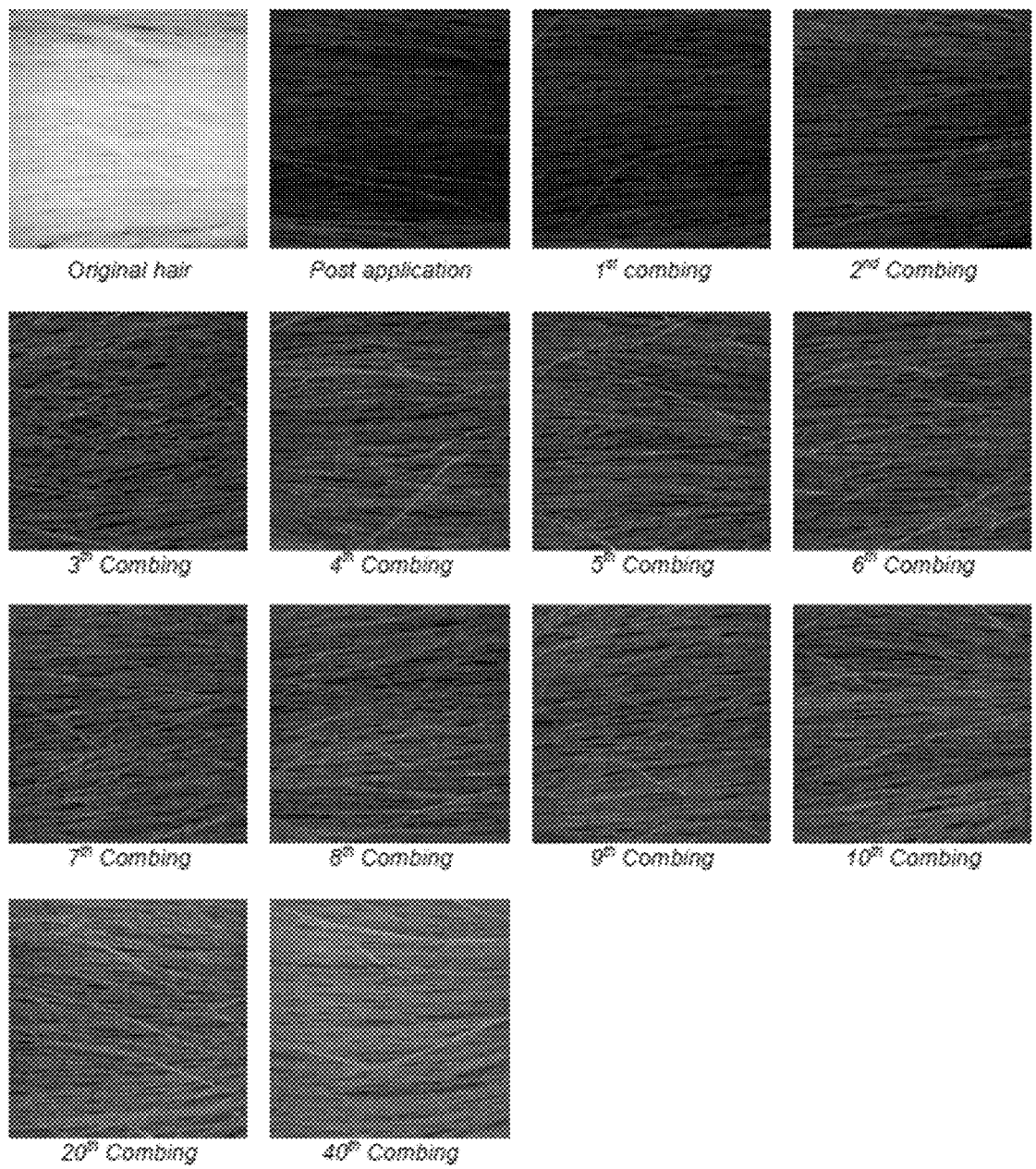
FIG. 4 is a series of high resolution images of a hair tress treated with a colored dry shampoo formulation according to an embodiment the present disclosure after several combings of the treated tress.

The treated tresses were each combed 10 times and high resolution images were captured after each of the 10 combings. The treated tresses were each combed another 10 times (20 total brushings) and high resolution images were captured. The treated tresses were each combed another 20 times (40 brushings total) and high resolution images were captured. FIG. 3 is a series of the high resolution images captured for the hair tress treated with the colored dry shampoo control formulation after the combings of the treated tress. FIG. 4 is a series of the high resolution images of the hair tress treated with a colored dry shampoo formulation according to an embodiment the present disclosure (Example 1) after several combings of the treated tress. Both the hair tress treated with the control formula and the hair tress treated with the Example 1 formula become lighter after each subsequent combing, however, the control sample lightens more rapidly.

Based on the high resolution images captured for the treated hair tresses, luminance L* values were calculated for each of the images (which were captured for 6 samples treated with the control formula and 6 samples treated with the Example 1 formula) and the mean values were computed. The luminance (L*) values for the samples after the combings are provided in Table 3 below.

TABLE 3

Luminance (L*) values for hair tresses treated with a control formula and hair tresses treated with the Example 1 formula after combings

| Product | Hair | Baseline | Post | 1 | 2 | 3 | 4 | 5 | 6 | 7 | 8 | 9 | 10 | 20 | 40 |
|---|---|---|---|---|---|---|---|---|---|---|---|---|---|---|---|
| Control | 1 | 82.26 | 14.04 | 27.52 | 38.61 | 43.79 | 44.37 | 48.32 | 49.21 | 49.02 | 49.79 | 51.36 | 52.13 | 56.35 | 61.92 |
|  | 2 | 81.79 | 29.69 | 30.00 | 34.73 | 40.58 | 41.40 | 43.97 | 44.96 | 44.98 | 46.04 | 46.82 | 47.41 | 53.91 | 57.75 |
|  | 3 | 81.01 | 27.95 | 29.75 | 37.97 | 40.82 | 41.53 | 44.94 | 46.07 | 46.99 | 48.50 | 48.06 | 49.47 | 54.51 | 58.97 |
|  | 4 | 81.53 | 17.09 | 22.61 | 33.21 | 39.92 | 42.23 | 44.46 | 47.65 | 48.53 | 50.12 | 50.69 | 51.17 | 55.55 | 60.75 |
|  | 5 | 84.22 | 19.75 | 22.64 | 35.40 | 46.86 | 48.81 | 49.71 | 53.63 | 54.91 | 55.54 | 55.32 | 58.02 | 59.18 | 61.54 |
|  | 6 | 81.08 | 24.28 | 27.32 | 35.12 | 42.16 | 44.29 | 47.85 | 45.71 | 48.09 | 50.06 | 50.42 | 50.70 | 56.32 | 61.19 |
| Example 1 | 1 | 81.06 | 8.21 | 13.12 | 18.20 | 21.97 | 22.67 | 24.10 | 24.19 | 26.05 | 26.59 | 26.61 | 27.19 | 32.87 | 41.11 |
|  | 2 | 84.47 | 9.44 | 11.84 | 22.39 | 26.53 | 27.58 | 29.98 | 32.03 | 33.28 | 33.35 | 32.69 | 33.73 | 36.68 | 42.44 |
|  | 3 | 81.13 | 14.51 | 18.43 | 24.20 | 27.10 | 29.83 | 30.49 | 31.86 | 33.79 | 34.88 | 35.37 | 37.14 | 40.33 | 43.75 |
|  | 4 | 82.40 | 18.67 | 22.62 | 24.26 | 26.34 | 30.99 | 31.51 | 31.36 | 34.40 | 34.31 | 34.72 | 36.92 | 40.49 | 45.03 |
|  | 5 | 80.54 | 9.85 | 12.07 | 18.15 | 20.00 | 21.93 | 25.90 | 25.57 | 27.96 | 28.76 | 28.21 | 29.01 | 35.34 | 43.65 |
|  | 6 | 81.53 | 11.69 | 13.39 | 16.17 | 21.94 | 22.62 | 28.02 | 27.25 | 28.19 | 27.84 | 29.60 | 29.93 | 37.23 | 43.76 |

Figure 5:
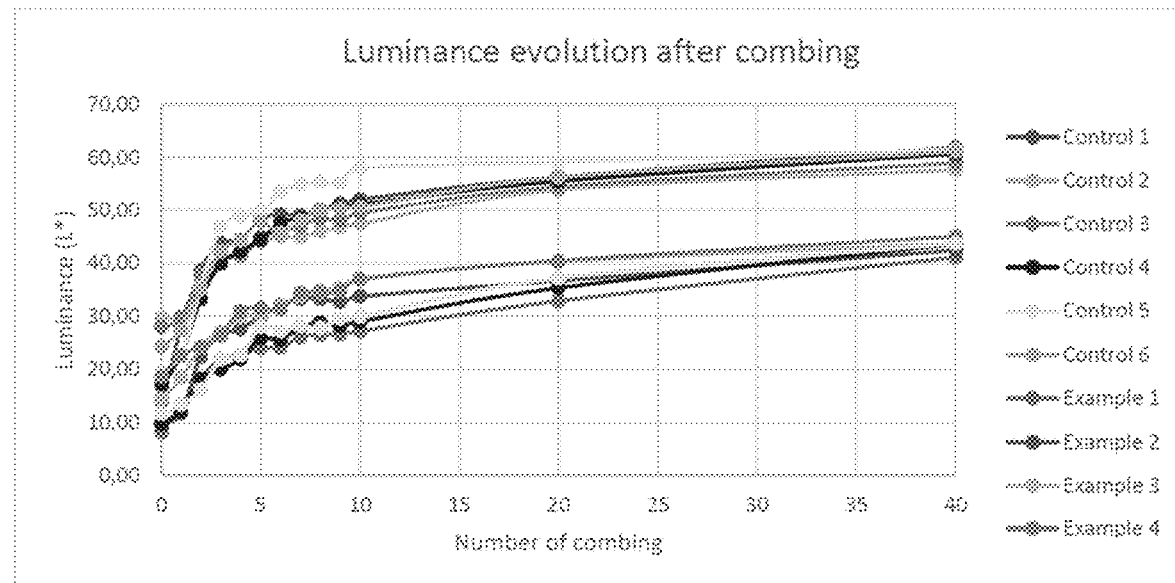
FIG. 5 is a plot of the Luminance evolution after combing for several samples treated with different colored dry shampoo compositions.

The values in Table 3 show a very good luminance consistency of the white hair tresses (before treatment with a colored dry shampoo formulation) that were used in this study. The Luminance values after application of the colored dry shampoo control formulation are higher than the luminance values after application of the colored dry shampoo Example 1 formulation. The higher luminance values indicate that less of the pigmented dry shampoo particles adhered to the hair tress. An increase of the luminance over time was also observed due to the reduction of the number of pigmented dry shampoo particles after combing. FIG. 5 is a plot of the luminance evolution after combing for each of the samples.

The quantity of dry shampoo particles adhered to the hair tress samples was correlated with the luminance values. Dry shampoo particles absorb emitting light, and thus it was assumed that the concentration of dry shampoo particles is proportional to the measured luminance. It was further estimated that the absorbance coefficient is very close for the two tested dry shampoo compositions (i.e., the control formulation and the Example 1 formulation). The quantity of remaining dry shampoo particles was thus determined based on the luminance values provided in Table 3 above, with product application considered as 100% of particle concentration and original white hair (without any product) considered as 0% particle concentration. Table 4 below shows the quantity of dry shampoo particles for each of the treated tresses after each combing.

From the statistical analysis, no significant difference was observed between the samples treated with the two formulations (i.e., Control formulation and Example 1 formulation) after the first shaking of the treated tress (i.e., combing number 1), but significant differences were observed after the first real combing.

In order to be more sensitive and, as after 40 combing, the luminance of the hair tress is still not close the initial

TABLE 4

Quantity of dry shampoo particles (%) for hair tresses treated with a control formula and hair tresses treated with the Example 1 formula after combings

| Product | Hair | Post | 1 | 2 | 3 | 4 | 5 | 6 | 7 | 8 | 9 | 10 | 20 | 40 |
|---|---|---|---|---|---|---|---|---|---|---|---|---|---|---|
| Control | 1 | 100% | 80% | 64% | 56% | 56% | 50% | 48% | 49% | 48% | 45% | 44% | 38% | 30% |
|  | 2 | 100% | 99% | 90% | 79% | 78% | 73% | 71% | 71% | 69% | 67% | 66% | 54% | 46% |
|  | 3 | 100% | 97% | 81% | 76% | 74% | 68% | 66% | 64% | 61% | 62% | 59% | 50% | 42% |
|  | 4 | 100% | 91% | 75% | 65% | 61% | 58% | 53% | 51% | 49% | 48% | 47% | 40% | 32% |
|  | 5 | 100% | 96% | 76% | 58% | 55% | 54% | 47% | 45% | 44% | 45% | 41% | 39% | 35% |
|  | 6 | 100% | 95% | 81% | 69% | 65% | 59% | 62% | 58% | 55% | 54% | 53% | 44% | 35% |
| Example 1 | 1 | 100% | 93% | 86% | 81% | 80% | 78% | 78% | 76% | 75% | 75% | 74% | 66% | 55% |
|  | 2 | 100% | 97% | 83% | 77% | 76% | 73% | 70% | 68% | 68% | 69% | 68% | 64% | 56% |
|  | 3 | 100% | 94% | 85% | 81% | 77% | 76% | 74% | 71% | 69% | 69% | 66% | 61% | 56% |
|  | 4 | 100% | 94% | 91% | 88% | 81% | 80% | 80% | 75% | 75% | 75% | 71% | 66% | 59% |
|  | 5 | 100% | 97% | 88% | 86% | 83% | 77% | 78% | 74% | 73% | 74% | 73% | 64% | 52% |
|  | 6 | 100% | 98% | 94% | 85% | 84% | 77% | 78% | 76% | 77% | 74% | 74% | 63% | 54% |

Figure 6:
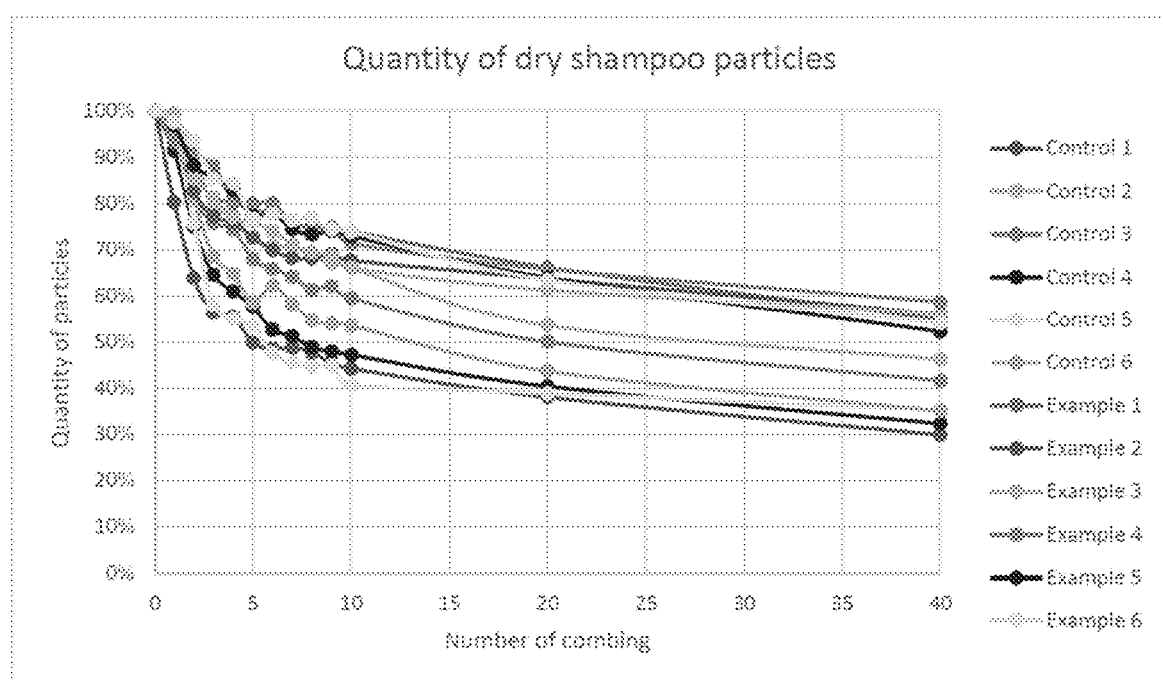
FIG. 6 is a plot of the quantity of dry shampoo particles after combing for several samples treated with different colored dry shampoo compositions.

FIG. 6 shows the quantity of dry shampoo particles after each combing for each of the samples tested. FIG. 1 is a plot of the average quantity of dry shampoo particles after each combing for the hair tresses treated with the control formulation and the average quantity of dry shampoo particles after each combing for the hair tresses treated with the Example 1 formulation. A strong decrease in the quantity of dry shampoo particles was observed after the first 4 combings for each of the two formulations, although the decrease was greater with the tresses treated with the control formulation. After the first four brushings, the decrease in the number of dry shampoo particles was almost linear until 10 brushings. The last brushings only had a small effect on the number of dry shampoo particles.

Table 5 below shows the statistical analysis for each of the time points (i.e., combing points) shown in FIG. 6. The p-value significance was defined under 0.05.

luminance without product (dry shampoo particles were visibly still remaining on the fibers), the luminance values were normalized with the last time point measurement (after 40 combing). In this analysis, the quantity of remaining dry shampoo particles was determined based on the luminance values with product application considered as 100% of particle concentration and after 40 combing as 0% of particle concentration. In this case, it was considered that the luminance after 40 combing was due to very thin colored particles that stay on the fibers and that cannot be removed with the combing method utilized. The normalized results are shown in Table 6 below.

TABLE 5

Statistical Analysis of the Quantity of Particles Data

| | | Quantity of particles | | | | | | | | | | |
|---|---|---|---|---|---|---|---|---|---|---|---|---|
| | Combing | 1 | 2 | 3 | 4 | 5 | 6 | 7 | 8 | 9 | 10 | 20 |
| Control | Mean | 93% | 78% | 67% | 65% | 60% | 58% | 56% | 54% | 54% | 52% | 44% |
| | Std | 6% | 8% | 8% | 9% | 8% | 9% | 9% | 8% | 9% | 9% | 6% |
| Example 1 | Mean | 95% | 88% | 83% | 80% | 77% | 76% | 73% | 73% | 73% | 71% | 64% |
| | Std | 2% | 4% | 4% | 3% | 2% | 3% | 3% | 3% | 3% | 3% | 2% |
| | Diff | −2% | −10% | −16% | −15% | −17% | −18% | −17% | −19% | −19% | −19% | −20% |
| | t-value | −0.849 | −2.577 | −3.911 | −3.763 | −4.555 | −4.326 | −4.103 | −4.661 | −4.787 | −4.581 | −7.421 |
| | p-value | 0.207 | 0.013 | 0.001 | 0.001 | >0.001 | >0.001 | >0.001 | >0.001 | >0.001 | >0.001 | >0.001 |
| | Significant | N | S | S | S | S | S | S | S | S | S | S |

TABLE 6

Normalized quantity of dry shampoo particles (%) for hair tresses treated with a
control formula and hair tresses treated with the Example 1 formula after combings

| Product | Hair | Post | 1 | 2 | 3 | 4 | 5 | 6 | 7 | 8 | 9 | 10 | 20 | 40 |
|---|---|---|---|---|---|---|---|---|---|---|---|---|---|---|
| Control | 1 | 100% | 72% | 49% | 38% | 37% | 28% | 27% | 27% | 25% | 22% | 20% | 12% | 0% |
|  | 2 | 100% | 99% | 82% | 61% | 58% | 49% | 46% | 45% | 42% | 39% | 37% | 14% | 0% |
|  | 3 | 100% | 94% | 68% | 59% | 56% | 45% | 42% | 39% | 34% | 35% | 31% | 14% | 0% |
|  | 4 | 100% | 87% | 63% | 48% | 42% | 37% | 30% | 28% | 24% | 23% | 22% | 12% | 0% |
|  | 5 | 100% | 93% | 63% | 35% | 30% | 28% | 19% | 16% | 14% | 15% | 8% | 6% | 0% |
|  | 6 | 100% | 92% | 71% | 52% | 46% | 36% | 42% | 35% | 30% | 29% | 28% | 13% | 0% |
| Example 1 | 1 | 100% | 85% | 70% | 58% | 56% | 52% | 51% | 46% | 44% | 44% | 42% | 25% | 0% |
|  | 2 | 100% | 93% | 61% | 48% | 45% | 38% | 32% | 28% | 28% | 30% | 26% | 17% | 0% |
|  | 3 | 100% | 87% | 67% | 57% | 48% | 45% | 41% | 34% | 30% | 29% | 23% | 12% | 0% |
|  | 4 | 100% | 85% | 79% | 71% | 53% | 51% | 52% | 40% | 41% | 39% | 31% | 17% | 0% |
|  | 5 | 100% | 93% | 75% | 70% | 64% | 53% | 53% | 46% | 44% | 46% | 43% | 25% | 0% |
|  | 6 | 100% | 95% | 86% | 68% | 66% | 49% | 51% | 49% | 50% | 44% | 43% | 20% | 0% |

With the normalized results, a strong decrease of the normalized quantity of dry shampoo particles after the first combing (40% remaining) was observed, and then a continuous decrease almost linearly until 10 brushings (22% particles remaining for the control-treated tresses and 36% of particles remaining for the Example 1-treated tresses) was observed. The difference between the two dry shampoo formulations becomes more apparent after the third coming for the normalized results.

In summary, the Example 1 formulation stays longer on the treated hair tresses than the control formulation. Accordingly, formulations prepared according to the present disclosure (i.e., including a hemisqualane) provide more long-lasting color effect than a dry shampoo composition which does not include a hemisqualane.

Example 3

The long-lasting color benefit provided by the composition of the present disclosure was evaluated.

A sample dry shampoo composition was prepared according to Example 1 above. A control sample was also prepared for comparison purposes. The control formula was prepared according to the method outlined in Example 1 above, except the control formula does not include any hemisqualanes. The control composition is provided in Table 2 above (with weight percentage ranges being based on the total weight of the respective dry shampoo composition).

After the Example 1 and control formulas were prepared, instrumental deposition analysis was used to analyze the long-lasting benefit of the two formulas. First, high resolution images of natural white hair tresses were captured. Next, each of the Example 1 formula and the control formula were applied to separate white hair tress samples. High resolution images of the treated hair tresses were captured after application of the dry shampoo formulas. A color chart was used to validate the color calibration parameters during the acquisition of the high resolution images. 30 samples were prepared for each of the two formulations. Similar to Example 2 above, the hair tresses treated with the control formulation had a higher luminance than the hair tresses treated with Example 1 formula.

The treated tresses were each combed 10 times and high resolution images were captured after each of the 10 combings. The treated tresses were each combed another 10 times (20 total brushings) and high resolution images were captured. The treated tresses were each combed another 20 times (40 brushings total) and high resolution images were captured. Similar to Example 2 above, both the hair tress treated with the control formula and the hair tress treated with the Example 1 formula become lighter after each subsequent combing, however, the control sample lightens more rapidly.

Based on the high resolution images captured for the treated hair tresses, luminance L* values were calculated (three repetitions for each of the brushings measured) for each of the images (which were captured for 30 samples treated with the control formula and 30 samples treated with the Example 1 formula) and the mean values were computed. The luminance (L*) values for the samples after the combings are provided in Table 7 below. Several hair tresses were removed because they were considered outliers.

TABLE 7

Luminance (L*) values for hair tresses treated with a control
formula and hair tresses treated with the Example 1 formula after combings

| Product | Hair tress | Baseline | Post | 1 | 2 | 3 | 4 | 5 | 6 | 7 | 8 | 9 | 10 | 20 | 40 |
|---|---|---|---|---|---|---|---|---|---|---|---|---|---|---|---|
| Control | 1 | 82.43 | 28.58 | 33.37 | 43.46 | 45.15 | 50.19 | 49.30 | 49.41 | 53.78 | 49.52 | 54.96 | 50.44 | 58.98 | 58.96 |
|  | 2 | 84.83 | 39.30 | 43.46 | 48.10 | 51.41 | 51.66 | 51.64 | 52.08 | 50.18 | 51.98 | 52.46 | 54.02 | 54.87 | 55.95 |
|  | 3 | 84.23 | 41.82 | 42.00 | 51.76 | 53.65 | 55.09 | 52.30 | 54.24 | 54.96 | 56.77 | 54.51 | 55.48 | 57.41 | 60.27 |
|  | 4 | 82.99 | 46.40 | 53.00 | 52.92 | 54.45 | 54.17 | 52.70 | 56.20 | 54.05 | 53.32 | 55.28 | 53.24 | 55.11 | 58.92 |
|  | 5 | 84.24 | 41.72 | 43.42 | 49.92 | 53.14 | 53.33 | 55.42 | 52.35 | 54.53 | 52.69 | 55.07 | 56.35 | 57.67 | 58.69 |
|  | 6 | 84.00 | 42.35 | 45.81 | 50.74 | 54.42 | 52.43 | 54.41 | 53.12 | 53.89 | 54.76 | 54.51 | 54.81 | 59.22 | 61.06 |
|  | 7 | 85.55 | 41.31 | 42.02 | 51.62 | 56.89 | 57.71 | 57.77 | 59.13 | 59.31 | 59.70 | 59.65 | 59.78 | 63.36 | 62.05 |
|  | 8 | 84.56 | 32.98 | 34.93 | 51.19 | 55.79 | 56.57 | 57.26 | 56.42 | 55.15 | 55.87 | 56.94 | 56.89 | 59.07 | 61.01 |

TABLE 7-continued

Luminance (L*) values for hair tresses treated with a control formula and hair tresses treated with the Example 1 formula after combings

| Product | Hair tress | Baseline | Post | 1 | 2 | 3 | 4 | 5 | 6 | 7 | 8 | 9 | 10 | 20 | 40 |
|---|---|---|---|---|---|---|---|---|---|---|---|---|---|---|---|
| | 9 | 84.24 | 37.11 | 37.40 | 42.66 | 45.64 | 47.90 | 48.75 | 51.10 | 51.70 | 52.18 | 51.80 | 52.40 | 55.03 | 58.60 |
| | 10 | 83.82 | 44.21 | 49.04 | 48.93 | 49.99 | 52.20 | 50.82 | 53.82 | 52.45 | 52.74 | 53.40 | 54.32 | 56.86 | 57.66 |
| | 11 | 83.92 | 44.63 | 51.40 | 53.72 | 53.98 | 56.31 | 56.72 | 58.17 | 58.70 | 57.58 | 58.80 | 58.60 | 58.13 | 61.34 |
| | 12 | 80.85 | 45.13 | 49.38 | 53.66 | 52.86 | 53.55 | 55.76 | 54.95 | 54.82 | 54.45 | 55.17 | 54.40 | 55.13 | 57.51 |
| | 13 | 83.41 | 43.49 | 50.82 | 55.96 | 54.51 | 55.39 | 56.45 | 57.01 | 55.74 | 56.09 | 58.26 | 59.25 | 60.54 | 57.88 |
| | 14 | 82.38 | 40.35 | 43.81 | 53.18 | 55.65 | 56.90 | 57.53 | 58.85 | 58.00 | 60.42 | 59.75 | 60.62 | 60.14 | 62.62 |
| | 15 | 80.83 | 39.55 | 44.13 | 46.29 | 52.04 | 51.36 | 53.28 | 53.57 | 56.72 | 54.21 | 55.20 | 54.22 | 55.89 | 60.89 |
| | 16 | 81.27 | 43.40 | 49.26 | 52.98 | 53.21 | 53.30 | 53.09 | 54.66 | 54.86 | 55.17 | 54.81 | 55.24 | 57.75 | 60.75 |
| | 17 | 82.54 | 42.20 | 48.20 | 51.23 | 53.28 | 53.35 | 53.59 | 55.37 | 55.28 | 55.43 | 55.17 | 55.50 | 58.82 | 61.74 |
| | 18 | 80.35 | 39.35 | 50.85 | 54.32 | 53.57 | 55.23 | 54.61 | 54.89 | 56.95 | 55.47 | 55.38 | 53.89 | 58.03 | 59.13 |
| | 19 | 78.58 | 45.75 | 50.65 | 48.40 | 48.57 | 48.09 | 49.33 | 49.18 | 49.20 | 50.36 | 49.27 | 50.53 | 51.65 | 55.02 |
| | 20 | 83.45 | 47.16 | 47.77 | 48.93 | 52.77 | 55.01 | 53.01 | 54.62 | 53.89 | 54.09 | 54.76 | 54.84 | 55.99 | 55.39 |
| | 21 | 74.93 | 42.99 | 49.06 | 55.93 | 55.03 | 55.75 | 55.51 | 56.59 | 56.92 | 55.91 | 57.12 | 56.04 | 57.64 | 58.87 |
| | 22 | 79.45 | 40.75 | 40.79 | 41.24 | 46.85 | 47.26 | 48.05 | 48.20 | 48.16 | 48.74 | 49.32 | 49.86 | 47.59 | 48.71 |
| | 23 | 80.86 | 40.73 | 45.70 | 52.38 | 52.01 | 52.53 | 53.01 | 54.24 | 54.43 | 56.42 | 56.08 | 57.76 | 57.07 | 60.77 |
| | 24 | 82.75 | 39.76 | 40.10 | 42.55 | 44.53 | 45.10 | 45.91 | 48.11 | 48.06 | 49.09 | 49.56 | 49.31 | 51.35 | 53.94 |
| | 25 | 80.55 | 38.95 | 43.22 | 44.59 | 46.95 | 47.98 | 49.42 | 51.19 | 51.55 | 51.73 | 52.74 | 52.12 | 53.20 | 53.54 |
| Example 1 | 1 | 84.25 | 16.83 | 30.26 | 33.47 | 34.76 | 35.97 | 35.65 | 38.08 | 39.89 | 39.46 | 40.96 | 48.14 | 49.56 | 53.70 |
| | 2 | 84.21 | 26.42 | 25.33 | 29.40 | 37.47 | 36.20 | 37.81 | 38.11 | 38.39 | 40.51 | 41.30 | 43.01 | 44.08 | 43.73 |
| | 3 | 84.35 | 26.12 | 29.49 | 32.15 | 34.77 | 35.15 | 36.64 | 35.00 | 37.66 | 37.78 | 36.96 | 40.96 | 40.59 | 44.49 |
| | 4 | 84.25 | 30.60 | 30.81 | 34.93 | 37.23 | 39.36 | 38.97 | 40.53 | 40.31 | 40.18 | 41.89 | 41.10 | 42.76 | 45.70 |
| | 5 | 82.66 | 27.62 | 28.29 | 33.82 | 35.12 | 36.42 | 37.92 | 37.53 | 39.66 | 41.01 | 40.56 | 42.16 | 42.75 | 46.94 |
| | 6 | 83.25 | 30.20 | 32.90 | 37.40 | 38.94 | 39.62 | 44.02 | 45.23 | 46.73 | 46.42 | 46.24 | 45.86 | 50.24 | 53.67 |
| | 7 | 83.70 | 27.98 | 27.35 | 34.09 | 33.90 | 39.49 | 40.03 | 37.29 | 40.70 | 41.70 | 41.53 | 40.95 | 43.73 | 49.26 |
| | 8 | 85.94 | 30.74 | 32.54 | 33.04 | 31.14 | 32.95 | 32.78 | 32.73 | 33.73 | 33.37 | 34.15 | 35.87 | 38.14 | 41.41 |
| | 9 | 85.37 | 19.88 | 23.57 | 27.42 | 28.19 | 29.30 | 30.65 | 31.23 | 31.62 | 31.29 | 32.65 | 33.97 | 35.75 | 40.24 |
| | 10 | 77.61 | 23.87 | 34.28 | 40.26 | 42.88 | 42.68 | 41.63 | 42.02 | 41.59 | 41.10 | 42.22 | 43.92 | 43.28 | 45.00 |
| | 11 | 82.83 | 30.88 | 40.81 | 40.51 | 40.38 | 39.41 | 40.36 | 39.53 | 39.48 | 41.35 | 41.73 | 40.90 | 41.95 | 42.65 |
| | 12 | 81.54 | 26.25 | 30.84 | 33.84 | 34.66 | 32.90 | 32.33 | 32.78 | 33.19 | 34.50 | 33.91 | 34.96 | 35.77 | 39.55 |
| | 13 | 80.03 | 31.65 | 36.19 | 39.17 | 39.85 | 39.36 | 40.65 | 38.39 | 40.81 | 42.19 | 41.54 | 43.37 | 42.17 | 43.94 |
| | 14 | 78.34 | 21.81 | 35.13 | 37.41 | 40.97 | 41.26 | 40.70 | 42.08 | 40.48 | 40.87 | 42.14 | 42.01 | 42.38 | 48.54 |
| | 15 | 79.58 | 22.26 | 22.81 | 31.82 | 31.75 | 33.18 | 36.90 | 38.03 | 38.48 | 39.16 | 40.71 | 41.86 | 45.68 | 46.68 |
| | 16 | 82.86 | 22.91 | 27.85 | 33.41 | 36.21 | 37.95 | 39.00 | 39.62 | 41.30 | 42.13 | 42.24 | 42.16 | 44.99 | 46.02 |
| | 17 | 80.27 | 19.15 | 19.52 | 35.25 | 37.63 | 41.92 | 40.99 | 43.20 | 44.21 | 44.35 | 44.43 | 45.30 | 47.28 | 48.52 |
| | 18 | 81.66 | 18.57 | 24.30 | 27.84 | 29.76 | 31.78 | 32.04 | 34.23 | 33.05 | 35.38 | 37.04 | 34.81 | 40.11 | 41.25 |
| | 19 | 81.47 | 24.86 | 29.71 | 34.40 | 34.22 | 34.49 | 34.11 | 34.78 | 34.07 | 35.85 | 36.36 | 35.92 | 37.92 | 48.89 |
| | 20 | 80.15 | 33.64 | 36.59 | 39.62 | 39.47 | 38.83 | 39.34 | 40.23 | 40.40 | 42.26 | 40.65 | 41.35 | 41.93 | 45.82 |
| | 21 | 83.18 | 22.16 | 32.48 | 34.69 | 38.28 | 37.34 | 36.89 | 37.39 | 35.87 | 35.81 | 36.28 | 37.85 | 38.62 | 43.45 |
| | 22 | 82.02 | 31.70 | 35.30 | 41.15 | 41.28 | 41.82 | 42.30 | 42.12 | 39.75 | 40.33 | 41.03 | 39.64 | 40.54 | 44.31 |
| | 23 | 81.39 | 32.84 | 35.68 | 40.12 | 39.05 | 39.76 | 39.81 | 39.67 | 39.68 | 39.28 | 40.50 | 42.80 | 43.98 | 45.88 |
| | 24 | 79.09 | 30.24 | 35.44 | 38.77 | 37.54 | 37.27 | 37.35 | 39.56 | 39.77 | 39.03 | 39.28 | 40.17 | 41.79 | 45.83 |
| | 25 | 80.68 | 25.78 | 34.58 | 37.87 | 37.14 | 39.05 | 37.68 | 38.80 | 37.37 | 37.67 | 40.33 | 38.45 | 42.20 | 44.57 |
| | 26 | 80.05 | 23.35 | 38.09 | 38.59 | 38.50 | 36.47 | 37.43 | 36.72 | 37.04 | 36.94 | 38.28 | 36.73 | 40.81 | 42.96 |
| | 27 | 83.07 | 19.40 | 22.62 | 33.63 | 31.67 | 34.02 | 32.47 | 33.44 | 34.88 | 36.29 | 35.30 | 37.29 | 41.49 | 43.46 |
| | 28 | 85.25 | 23.27 | 26.69 | 28.26 | 29.25 | 32.02 | 30.74 | 33.98 | 32.17 | 34.15 | 34.70 | 32.82 | 34.80 | 42.10 |
| | 29 | 81.84 | 28.07 | 31.73 | 32.76 | 34.50 | 34.80 | 35.29 | 36.33 | 36.62 | 37.47 | 39.22 | 40.47 | 42.36 | 51.68 |

The values in Table 7 show a very good luminance consistency of the white hair tresses (before treatment with a colored dry shampoo formulation) that were used in this study with an average L* value of 82. Similar to Example 2 above, the Luminance values after application of the colored dry shampoo control formulation are higher than the luminance values after application of the colored dry shampoo Example 1 formulation. The higher luminance values indicate that less of the pigmented dry shampoo particles adhered to the hair tress. An increase of the luminance over time was also observed due to the reduction of the number of pigmented dry shampoo particles after combing.

The quantity of dry shampoo particles adhered to the hair tress samples was correlated with the luminance values. Dry shampoo particles absorb emitting light, and thus it was assumed that the concentration of dry shampoo particles is proportional to the measured luminance. It was further estimated that the absorbance coefficient is very close for the two tested dry shampoo compositions (i.e., the control formulation and the Example 1 formulation). The quantity of remaining dry shampoo particles was thus determined based on the luminance values provided in Table 3 above, with product application considered as 100% of particle concentration and original white hair (without any product) considered as 0% particle concentration. Table 8 below shows the quantity of dry shampoo particles for each of the treated tresses after each combing.

TABLE 8

Quantity of dry shampoo particles (%) for hair tresses treated with a control formula and hair tresses treated with the Example 1 formula after combings

| Product | Hair tress | Post | 1 | 2 | 3 | 4 | 5 | 6 | 7 | 8 | 9 | 10 | 20 | 40 |
|---|---|---|---|---|---|---|---|---|---|---|---|---|---|---|---|
| Control | 1 | 100% | 91% | 72% | 69% | 60% | 62% | 61% | 53% | 61% | 51% | 59% | 44% | 44% |
| | 2 | 100% | 91% | 81% | 73% | 73% | 73% | 72% | 76% | 72% | 71% | 68% | 66% | 63% |
| | 3 | 100% | 100% | 77% | 72% | 69% | 75% | 71% | 69% | 65% | 70% | 68% | 63% | 57% |
| | 4 | 100% | 82% | 82% | 78% | 79% | 83% | 73% | 79% | 81% | 76% | 81% | 76% | 66% |
| | 5 | 100% | 96% | 81% | 73% | 73% | 68% | 75% | 70% | 74% | 69% | 66% | 62% | 60% |
| | 6 | 100% | 92% | 80% | 71% | 76% | 71% | 74% | 72% | 70% | 71% | 70% | 60% | 55% |
| | 7 | 100% | 98% | 77% | 65% | 63% | 63% | 60% | 59% | 58% | 59% | 58% | 50% | 53% |
| | 8 | 100% | 96% | 65% | 56% | 54% | 53% | 55% | 57% | 56% | 54% | 54% | 49% | 46% |
| | 9 | 100% | 99% | 88% | 82% | 77% | 75% | 70% | 69% | 68% | 69% | 68% | 62% | 54% |
| | 10 | 100% | 88% | 88% | 85% | 80% | 83% | 76% | 79% | 78% | 77% | 74% | 68% | 66% |
| | 11 | 100% | 83% | 77% | 76% | 70% | 69% | 66% | 64% | 67% | 64% | 64% | 66% | 57% |
| | 12 | 100% | 88% | 76% | 78% | 76% | 70% | 73% | 73% | 74% | 72% | 74% | 72% | 65% |
| | 13 | 100% | 82% | 69% | 72% | 70% | 68% | 66% | 69% | 68% | 63% | 61% | 57% | 64% |
| | 14 | 100% | 92% | 69% | 64% | 61% | 59% | 56% | 58% | 52% | 54% | 52% | 53% | 47% |
| | 15 | 100% | 89% | 84% | 70% | 71% | 67% | 66% | 58% | 64% | 62% | 64% | 60% | 48% |
| | 16 | 100% | 85% | 75% | 74% | 74% | 74% | 70% | 70% | 69% | 70% | 69% | 62% | 54% |
| | 17 | 100% | 85% | 78% | 73% | 72% | 72% | 67% | 68% | 67% | 68% | 67% | 59% | 52% |
| | 18 | 100% | 72% | 63% | 65% | 61% | 63% | 62% | 57% | 61% | 61% | 65% | 54% | 52% |
| | 19 | 100% | 85% | 92% | 91% | 93% | 89% | 90% | 89% | 86% | 89% | 85% | 82% | 72% |
| | 20 | 100% | 98% | 95% | 85% | 78% | 84% | 79% | 81% | 81% | 79% | 79% | 76% | 77% |
| | 21 | 100% | 81% | 59% | 62% | 60% | 61% | 57% | 56% | 60% | 56% | 59% | 54% | 50% |
| | 22 | 100% | 100% | 99% | 84% | 83% | 81% | 81% | 81% | 79% | 78% | 76% | 82% | 79% |
| | 23 | 100% | 88% | 71% | 72% | 71% | 69% | 66% | 66% | 61% | 62% | 58% | 59% | 50% |
| | 24 | 100% | 99% | 94% | 89% | 88% | 86% | 81% | 81% | 78% | 77% | 78% | 73% | 67% |
| | 25 | 100% | 90% | 86% | 81% | 78% | 75% | 71% | 70% | 69% | 67% | 68% | 66% | 65% |
| Example 1 | 1 | 100% | 80% | 75% | 73% | 72% | 72% | 68% | 66% | 66% | 64% | 54% | 51% | 45% |
| | 2 | 100% | 102% | 95% | 81% | 83% | 80% | 80% | 79% | 76% | 74% | 71% | 69% | 70% |
| | 3 | 100% | 94% | 90% | 85% | 84% | 82% | 85% | 80% | 80% | 81% | 75% | 75% | 68% |
| | 4 | 100% | 100% | 92% | 88% | 84% | 84% | 81% | 82% | 82% | 79% | 80% | 77% | 72% |
| | 5 | 100% | 99% | 89% | 86% | 84% | 81% | 82% | 78% | 76% | 76% | 74% | 73% | 65% |
| | 6 | 100% | 95% | 86% | 84% | 82% | 74% | 72% | 69% | 69% | 70% | 70% | 62% | 56% |
| | 7 | 100% | 101% | 89% | 89% | 79% | 78% | 83% | 77% | 75% | 76% | 77% | 72% | 62% |
| | 8 | 100% | 97% | 96% | 99% | 96% | 96% | 96% | 95% | 95% | 94% | 91% | 87% | 81% |
| | 9 | 100% | 94% | 88% | 87% | 86% | 84% | 83% | 82% | 83% | 81% | 78% | 76% | 69% |
| | 10 | 100% | 81% | 69% | 65% | 65% | 67% | 66% | 67% | 68% | 66% | 63% | 64% | 61% |
| | 11 | 100% | 81% | 81% | 82% | 84% | 82% | 83% | 83% | 80% | 79% | 81% | 79% | 77% |
| | 12 | 100% | 92% | 86% | 85% | 88% | 89% | 88% | 87% | 85% | 86% | 84% | 83% | 76% |
| | 13 | 100% | 91% | 84% | 83% | 84% | 81% | 86% | 81% | 78% | 80% | 76% | 78% | 75% |
| | 14 | 100% | 76% | 72% | 66% | 66% | 67% | 64% | 67% | 66% | 64% | 64% | 64% | 53% |
| | 15 | 100% | 99% | 83% | 83% | 81% | 74% | 72% | 72% | 71% | 68% | 66% | 59% | 57% |
| | 16 | 100% | 92% | 82% | 78% | 75% | 73% | 72% | 69% | 68% | 68% | 68% | 63% | 61% |
| | 17 | 100% | 99% | 74% | 70% | 63% | 64% | 61% | 59% | 59% | 59% | 57% | 54% | 52% |
| | 18 | 100% | 91% | 85% | 82% | 79% | 79% | 75% | 77% | 73% | 71% | 74% | 66% | 64% |
| | 19 | 100% | 91% | 83% | 83% | 83% | 84% | 82% | 84% | 81% | 80% | 80% | 77% | 58% |
| | 20 | 100% | 94% | 87% | 87% | 89% | 88% | 86% | 85% | 81% | 85% | 83% | 82% | 74% |
| | 21 | 100% | 83% | 79% | 74% | 75% | 76% | 75% | 78% | 78% | 77% | 74% | 73% | 65% |
| | 22 | 100% | 93% | 81% | 81% | 80% | 79% | 79% | 84% | 83% | 81% | 84% | 82% | 75% |
| | 23 | 100% | 94% | 85% | 87% | 86% | 86% | 86% | 86% | 87% | 84% | 79% | 77% | 73% |
| | 24 | 100% | 89% | 83% | 85% | 86% | 85% | 81% | 80% | 82% | 81% | 80% | 76% | 68% |
| | 25 | 100% | 84% | 78% | 79% | 76% | 78% | 76% | 79% | 78% | 74% | 77% | 70% | 66% |
| | 26 | 100% | 74% | 73% | 73% | 77% | 75% | 76% | 76% | 76% | 74% | 76% | 69% | 65% |
| | 27 | 100% | 95% | 78% | 81% | 77% | 79% | 78% | 76% | 73% | 75% | 72% | 65% | 62% |
| | 28 | 100% | 94% | 92% | 90% | 86% | 88% | 83% | 86% | 82% | 82% | 85% | 81% | 70% |
| | 29 | 100% | 93% | 91% | 88% | 87% | 87% | 85% | 84% | 83% | 79% | 77% | 73% | 56% |

Similar to Example 2 above, a strong decrease in the quantity of dry shampoo particles was observed after the first 4 combings for each of the two formulations, although the decrease was greater with the tresses treated with the control formulation. After the first four brushings, the decrease in the number of dry shampoo particles was almost linear until 10 brushings. The last brushings only had a small effect on the number of dry shampoo particles.

Table 9 below shows the statistical analysis for each of the time points (i.e., combing points). The p-value significance was defined under 0.05.

TABLE 9

Statistical Analysis of the Quantity of Particles Data

| | | Quantity of particles | | | | | | | | | | | |
|---|---|---|---|---|---|---|---|---|---|---|---|---|---|
| | Combing | 1 | 2 | 3 | 4 | 5 | 6 | 7 | 8 | 9 | 10 | 20 | 40 |
| Control | Mean | 90% | 79% | 74% | 72% | 72% | 69% | 69% | 69% | 67% | 67% | 63% | 59% |
| | Std | 7% | 10% | 9% | 9% | 9% | 8% | 9% | 9% | 9% | 8% | 10% | 9% |
| Example 1 | Mean | 91% | 84% | 82% | 81% | 80% | 79% | 78% | 77% | 76% | 75% | 72% | 65% |
| | Std | 7% | 7% | 8% | 7% | 7% | 8% | 8% | 8% | 8% | 8% | 9% | 8% |
| | Diff | −1% | −5% | −7% | −8% | −8% | −9% | −9% | −8% | −9% | −7% | −9% | −7% |
| | p-value | 0.242 | 0.031 | 0.001 | 0.001 | 0.001 | 0.000 | 0.000 | 0.000 | 0.000 | 0.002 | 0.001 | 0.007 |
| | significant | N | S | S | S | S | S | S | S | S | S | S | S |

From the statistical analysis, no significant difference was observed between the samples treated with the two formulations (i.e., Control formulation and Example 1 formulation) after the first shaking of the treated tress (i.e., combing number 1), but significant differences were observed after the first real combing.

In order to be more sensitive and, as after 40 combing, the luminance of the hair tress is still not close the initial luminance without product (dry shampoo particles were visibly still remaining on the fibers), the luminance values were normalized with the last time point measurement (after 40 combing) similar to Example 2 above. In this analysis, the quantity of remaining dry shampoo particles was determined based on the luminance values with product application considered as 100% of particle concentration and after 40 combing as 0% of particle concentration. In this case, it was considered that the luminance after 40 combing was due to very thin colored particles that stay on the fibers and that cannot be removed with the combing method utilized.

With the normalized results, a strong decrease of the normalized quantity of dry shampoo particles after the first combing (40% remaining) was observed, and then a continuous decrease almost linearly until 10 brushings (21% particles remaining for the control-treated tresses and 28% of particles remaining for the Example 1-treated tresses) was observed. The difference between the two dry shampoo formulations becomes more apparent after the third coming for the normalized results. The statistical analysis for the normalized results for each of the time points (i.e., combing points) are shown in Table 10 below. The p-value significance was defined under 0.05.

TABLE 10

Statistical analysis for normalized quantity of dry shampoo particles (%) for hair tresses treated with a control formula and hair tresses treated with the Example 1 formula after combings

| | | Normalized quantity of particles | | | | | | | | | | |
|---|---|---|---|---|---|---|---|---|---|---|---|---|
| | Combing | 1 | 2 | 3 | 4 | 5 | 6 | 7 | 8 | 9 | 10 | 20 |
| Control | Mean | 76% | 52% | 39% | 34% | 32% | 26% | 26% | 25% | 21% | 21% | 11% |
| | Std | 18% | 19% | 13% | 15% | 14% | 13% | 13% | 11% | 14% | 14% | 12% |
| Example 1 | Mean | 74% | 53% | 48% | 44% | 42% | 40% | 38% | 34% | 31% | 28% | 19% |
| | Std | 22% | 18% | 19% | 16% | 15% | 15% | 13% | 14% | 14% | 14% | 12% |
| | Diff | 1% | −1% | −9% | −11% | −10% | −14% | −12% | −9% | −10% | −7% | −8% |
| | p-value | 0.432 | 0.425 | 0.024 | 0.009 | 0.010 | 0.000 | 0.001 | 0.005 | 0.006 | 0.027 | 0.014 |
| | significant | N | N | S | S | S | S | S | S | S | S | S |

Figure 7:
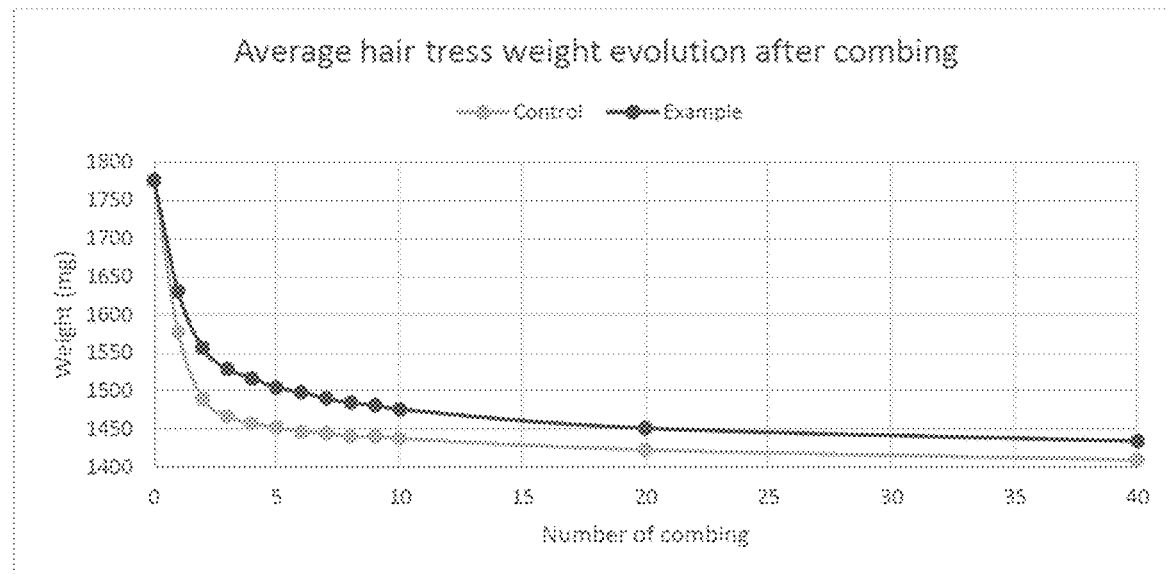
FIG. 7 is a plot of the average hair tress weight after combing for several samples treated with different colored dry shampoo compositions.

A high precision scale was used to measure the weight of the hair tress after each combing. The sensibility of the scale was 1 mg. The scale was calibrated before each hair tress measurement and the 0 calibration was done every measurement to ensure that the particles that fell on the plate during the process were not considered in the readings. Table 11 below shows the hair tress weight (mg) for each time point. FIG. 7 is a plot showing the average hair tress weight at each of the combings.

TABLE 11

Hair tress weight (mg)

| Product | Hair tress | No product | Post | 1 | 2 | 3 | 4 | 5 | 6 | 7 | 8 | 9 | 10 | 20 | 40 |
|---|---|---|---|---|---|---|---|---|---|---|---|---|---|---|---|
| Control | 1 | 1390 | 1724 | 1618 | 1472 | 1451 | 1446 | 1435 | 1432 | 1431 | 1430 | 1424 | 1432 | 1426 | 1425 |
| | 2 | 1512 | 2211 | 1975 | 1740 | 1707 | 1695 | 1663 | 1653 | 1646 | 1641 | 1635 | 1612 | 1608 | 1590 |
| | 3 | 1395 | 1887 | 1688 | 1515 | 1486 | 1463 | 1459 | 1445 | 1440 | 1416 | 1437 | 1435 | 1430 | 1403 |
| | 4 | 1492 | 1979 | 1815 | 1716 | 1701 | 1696 | 1690 | 1689 | 1674 | 1663 | 1667 | 1665 | 1660 | 1630 |
| | 5 | 1463 | 1844 | 1627 | 1517 | 1495 | 1506 | 1522 | 1515 | 1546 | 1544 | 1512 | 1511 | 1510 | 1506 |
| | 6 | 1368 | 1823 | 1666 | 1534 | 1483 | 1481 | 1455 | 1432 | 1455 | 1446 | 1447 | 1442 | 1412 | 1389 |
| | 7 | 1402 | 1902 | 1733 | 1630 | 1603 | 1586 | 1578 | 1556 | 1552 | 1550 | 1549 | 1548 | 1520 | 1468 |
| | 8 | 1401 | 1924 | 1768 | 1606 | 1567 | 1540 | 1541 | 1539 | 1532 | 1531 | 1530 | 1531 | 1497 | 1492 |
| | 9 | 1434 | 1811 | 1684 | 1580 | 1570 | 1532 | 1527 | 1522 | 1519 | 1515 | 1521 | 1513 | 1461 | 1450 |
| | 10 | 1355 | 1778 | 1570 | 1493 | 1456 | 1441 | 1437 | 1433 | 1429 | 1425 | 1420 | 1420 | 1380 | 1368 |
| | 11 | 1336 | 1773 | 1558 | 1512 | 1459 | 1452 | 1450 | 1405 | 1381 | 1382 | 1479 | 1472 | 1460 | 1353 |
| | 12 | 1417 | 1904 | 1532 | 1496 | 1490 | 1488 | 1486 | 1483 | 1481 | 1479 | 1477 | 1476 | 1470 | 1466 |
| | 13 | 1103 | 1475 | 1160 | 1156 | 1155 | 1153 | 1152 | 1150 | 1148 | 1147 | 1145 | 1144 | 1140 | 1135 |
| | 14 | 1270 | 1743 | 1382 | 1345 | 1332 | 1326 | 1322 | 1320 | 1318 | 1317 | 1315 | 1310 | 1280 | 1290 |
| | 15 | 1307 | 1703 | 1585 | 1390 | 1386 | 1376 | 1374 | 1372 | 1370 | 1366 | 1364 | 1363 | 1359 | 1355 |
| | 16 | 1102 | 1657 | 1447 | 1318 | 1292 | 1281 | 1275 | 1274 | 1270 | 1266 | 1239 | 1234 | 1201 | 1136 |
| | 17 | 1300 | 1887 | 1694 | 1530 | 1470 | 1460 | 1445 | 1440 | 1425 | 1395 | 1384 | 1380 | 1354 | 1350 |
| | 18 | 1305 | 1755 | 1499 | 1420 | 1388 | 1386 | 1384 | 1382 | 1382 | 1380 | 1369 | 1365 | 1349 | 1334 |
| | 19 | 1398 | 1882 | 1705 | 1608 | 1559 | 1534 | 1508 | 1507 | 1505 | 1502 | 1500 | 1499 | 1492 | 1487 |
| | 20 | 1370 | 1712 | 1533 | 1448 | 1440 | 1428 | 1440 | 1427 | 1437 | 1430 | 1428 | 1420 | 1386 | 1402 |
| | 21 | 1378 | 1669 | 1531 | 1464 | 1439 | 1422 | 1421 | 1420 | 1419 | 1419 | 1418 | 1416 | 1410 | 1402 |
| | 22 | 1475 | 1747 | 1523 | 1512 | 1511 | 1510 | 1510 | 1510 | 1508 | 1507 | 1505 | 1504 | 1490 | 1485 |
| | 23 | 1422 | 1691 | 1573 | 1550 | 1548 | 1538 | 1534 | 1528 | 1532 | 1532 | 1530 | 1522 | 1521 | 1520 |
| | 24 | 1455 | 1754 | 1565 | 1536 | 1531 | 1528 | 1524 | 1521 | 1522 | 1519 | 1517 | 1519 | 1512 | 1511 |
| | 25 | 1480 | 1756 | 1601 | 1573 | 1568 | 1563 | 1562 | 1562 | 1560 | 1560 | 1558 | 1560 | 1551 | 1548 |
| | 26 | 1296 | 1622 | 1404 | 1353 | 1344 | 1341 | 1339 | 1342 | 1337 | 1336 | 1339 | 1331 | 1326 | 1320 |
| | 27 | 1401 | 1663 | 1502 | 1486 | 1480 | 1476 | 1477 | 1474 | 1475 | 1470 | 1469 | 1468 | 1464 | 1462 |
| | 28 | 1314 | 1623 | 1454 | 1384 | 1365 | 1354 | 1351 | 1347 | 1342 | 1342 | 1343 | 1345 | 1335 | 1330 |
| | 29 | 1349 | 1691 | 1507 | 1493 | 1440 | 1439 | 1430 | 1429 | 1427 | 1425 | 1424 | 1422 | 1413 | 1410 |
| | 30 | 1260 | 1720 | 1423 | 1311 | 1292 | 1292 | 1288 | 1286 | 1284 | 1283 | 1282 | 1281 | 1279 | 1275 |
| Example 1 | 1 | 1538 | 1860 | 1841 | 1780 | 1761 | 1734 | 1711 | 1692 | 1675 | 1670 | 1657 | 1653 | 1648 | 1642 |
| | 2 | 1402 | 1849 | 1690 | 1636 | 1622 | 1602 | 1586 | 1569 | 1565 | 1535 | 1555 | 1549 | 1505 | 1499 |
| | 3 | 1314 | 1799 | 1683 | 1551 | 1520 | 1487 | 1483 | 1469 | 1455 | 1446 | 1441 | 1401 | 1396 | 1390 |
| | 4 | 1425 | 1897 | 1766 | 1608 | 1600 | 1577 | 1570 | 1551 | 1545 | 1541 | 1539 | 1524 | 1493 | 1470 |
| | 5 | 1427 | 1856 | 1760 | 1690 | 1662 | 1658 | 1650 | 1647 | 1642 | 1636 | 1627 | 1624 | 1601 | 1568 |
| | 6 | 1288 | 1637 | 1563 | 1483 | 1446 | 1434 | 1423 | 1417 | 1412 | 1406 | 1393 | 1389 | 1376 | 1363 |
| | 7 | 1380 | 1742 | 1653 | 1556 | 1508 | 1502 | 1492 | 1485 | 1480 | 1476 | 1473 | 1470 | 1459 | 1444 |
| | 8 | 1549 | 2018 | 1891 | 1807 | 1761 | 1732 | 1715 | 1702 | 1694 | 1681 | 1679 | 1676 | 1644 | 1619 |
| | 9 | 1542 | 1958 | 1907 | 1889 | 1861 | 1841 | 1827 | 1806 | 1794 | 1783 | 1776 | 1765 | 1719 | 1685 |
| | 10 | 1520 | 2090 | 1996 | 1918 | 1856 | 1825 | 1807 | 1798 | 1787 | 1776 | 1769 | 1758 | 1705 | 1645 |
| | 11 | 1400 | 1630 | 1535 | 1473 | 1470 | 1442 | 1444 | 1462 | 1455 | 1445 | 1444 | 1443 | 1421 | 1421 |
| | 12 | 1371 | 1712 | 1544 | 1506 | 1492 | 1490 | 1470 | 1460 | 1458 | 1476 | 1462 | 1460 | 1446 | 1438 |
| | 13 | 1320 | 1792 | 1614 | 1496 | 1491 | 1470 | 1455 | 1453 | 1452 | 1427 | 1433 | 1430 | 1404 | 1372 |
| | 14 | 1347 | 1647 | 1480 | 1432 | 1422 | 1413 | 1411 | 1403 | 1402 | 1404 | 1403 | 1383 | 1370 | 1362 |
| | 15 | 1252 | 1610 | 1472 | 1375 | 1372 | 1334 | 1322 | 1335 | 1318 | 1332 | 1293 | 1329 | 1280 | 1269 |
| | 16 | 1250 | 1723 | 1626 | 1452 | 1421 | 1412 | 1406 | 1391 | 1390 | 1386 | 1384 | 1382 | 1338 | 1330 |
| | 17 | 1180 | 1579 | 1441 | 1323 | 1290 | 1287 | 1286 | 1285 | 1253 | 1255 | 1283 | 1282 | 1281 | 1269 |
| | 18 | 1207 | 1600 | 1413 | 1350 | 1336 | 1326 | 1311 | 1297 | 1290 | 1289 | 1281 | 1280 | 1279 | 1268 |
| | 19 | 1328 | 1797 | 1649 | 1513 | 1499 | 1492 | 1490 | 1442 | 1440 | 1441 | 1435 | 1435 | 1430 | 1426 |
| | 20 | 1380 | 1741 | 1623 | 1550 | 1486 | 1511 | 1494 | 1495 | 1470 | 1469 | 1465 | 1420 | 1418 | 1407 |
| | 21 | 1285 | 1588 | 1373 | 1334 | 1331 | 1330 | 1329 | 1327 | 1325 | 1325 | 1324 | 1324 | 1318 | 1313 |
| | 22 | 1486 | 1848 | 1634 | 1638 | 1562 | 1622 | 1577 | 1596 | 1581 | 1606 | 1580 | 1593 | 1523 | 1533 |
| | 23 | 1330 | 1623 | 1440 | 1370 | 1360 | 1370 | 1366 | 1365 | 1373 | 1352 | 1350 | 1348 | 1356 | 1353 |
| | 24 | 1280 | 1667 | 1414 | 1401 | 1396 | 1392 | 1390 | 1387 | 1384 | 1381 | 1380 | 1378 | 1366 | 1331 |
| | 25 | 1357 | 1681 | 1416 | 1414 | 1413 | 1412 | 1410 | 1409 | 1407 | 1404 | 1402 | 1400 | 1392 | 1377 |
| | 26 | 1275 | 1747 | 1493 | 1451 | 1441 | 1395 | 1389 | 1453 | 1436 | 1383 | 1425 | 1429 | 1369 | 1329 |
| | 27 | 1266 | 1633 | 1404 | 1380 | 1355 | 1345 | 1331 | 1312 | 1310 | 1308 | 1306 | 1302 | 1297 | 1293 |
| | 28 | 1380 | 1808 | 1663 | 1601 | 1554 | 1538 | 1521 | 1506 | 1502 | 1498 | 1496 | 1484 | 1443 | 1415 |
| | 29 | 1546 | 2061 | 1979 | 1891 | 1825 | 1793 | 1756 | 1746 | 1734 | 1726 | 1715 | 1708 | 1648 | 1611 |
| | 30 | 1530 | 2073 | 1966 | 1815 | 1752 | 1730 | 1710 | 1694 | 1682 | 1677 | 1667 | 1660 | 1616 | 1588 |

The evolution of the average weight of the hair tresses is similar to the particles quantity analysis. In summary, the Example 1 formulation stays longer on the treated hair tresses than the control formulation, which is easier to remove even after the first combing.

Figure 8:
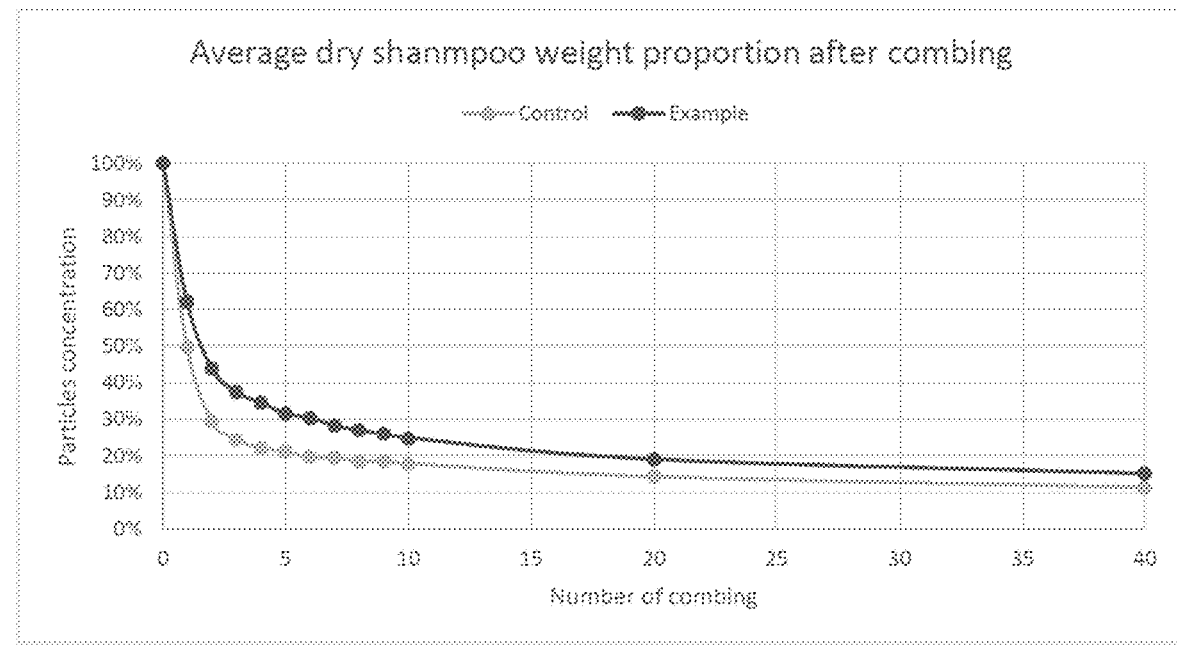
FIG. 8 is a plot showing the average dry shampoo weight proportion after combing for several samples treated with different colored dry shampoo compositions.

The weight of the dry shampoo and the concentration (based on the weight) of the remaining particles was analyzed. Table 12 below shows the normalized remaining particles weight values. FIG. 8 is a plot showing the average dry shampoo weight proportion at each of the combings.

TABLE 12

Normalized remaining particles weight (mg)

| Product | Hair tress | Post | 1 | 2 | 3 | 4 | 5 | 6 | 7 | 8 | 9 | 10 | 20 | 40 |
|---|---|---|---|---|---|---|---|---|---|---|---|---|---|---|
| Control | 1 | 100% | 68% | 25% | 18% | 17% | 13% | 13% | 12% | 12% | 10% | 13% | 11% | 10% |
| | 2 | 100% | 66% | 33% | 28% | 26% | 22% | 20% | 19% | 18% | 18% | 14% | 14% | 11% |
| | 3 | 100% | 60% | 24% | 18% | 14% | 13% | 10% | 9% | 4% | 9% | 8% | 7% | 2% |
| | 4 | 100% | 66% | 46% | 43% | 42% | 41% | 40% | 37% | 35% | 36% | 36% | 34% | 28% |
| | 5 | 100% | 43% | 14% | 8% | 11% | 15% | 14% | 22% | 21% | 13% | 13% | 12% | 11% |
| | 6 | 100% | 65% | 36% | 25% | 25% | 19% | 14% | 19% | 17% | 17% | 16% | 10% | 5% |
| | 7 | 100% | 66% | 46% | 40% | 37% | 35% | 31% | 30% | 30% | 29% | 29% | 24% | 13% |
| | 8 | 100% | 70% | 39% | 32% | 27% | 27% | 26% | 25% | 25% | 25% | 25% | 18% | 17% |
| | 9 | 100% | 66% | 39% | 36% | 26% | 25% | 23% | 23% | 21% | 23% | 21% | 7% | 4% |
| | 10 | 100% | 51% | 33% | 24% | 20% | 19% | 18% | 17% | 17% | 15% | 15% | 6% | 3% |
| | 11 | 100% | 51% | 40% | 28% | 27% | 26% | 16% | 10% | 11% | 33% | 31% | 28% | 4% |
| | 12 | 100% | 24% | 16% | 15% | 15% | 14% | 14% | 13% | 13% | 12% | 12% | 11% | 10% |
| | 13 | 100% | 15% | 14% | 14% | 13% | 13% | 13% | 12% | 12% | 11% | 11% | 10% | 9% |
| | 14 | 100% | 24% | 16% | 13% | 12% | 11% | 11% | 10% | 10% | 10% | 8% | 2% | 4% |
| | 15 | 100% | 70% | 21% | 20% | 17% | 17% | 16% | 16% | 15% | 14% | 14% | 13% | 12% |
| | 16 | 100% | 62% | 39% | 34% | 32% | 31% | 31% | 30% | 30% | 25% | 24% | 18% | 6% |
| | 17 | 100% | 67% | 39% | 29% | 27% | 25% | 24% | 21% | 16% | 14% | 14% | 9% | 9% |
| | 18 | 100% | 43% | 26% | 18% | 18% | 18% | 17% | 17% | 17% | 14% | 13% | 10% | 6% |
| | 19 | 100% | 63% | 43% | 33% | 28% | 23% | 23% | 22% | 21% | 21% | 21% | 19% | 18% |
| | 20 | 100% | 48% | 23% | 20% | 17% | 20% | 17% | 20% | 18% | 17% | 15% | 5% | 9% |
| | 21 | 100% | 53% | 30% | 21% | 15% | 15% | 14% | 14% | 14% | 14% | 13% | 11% | 8% |
| | 22 | 100% | 18% | 14% | 13% | 13% | 13% | 13% | 12% | 12% | 11% | 11% | 6% | 4% |
| | 23 | 100% | 56% | 48% | 47% | 43% | 42% | 39% | 41% | 41% | 40% | 37% | 37% | 36% |
| | 24 | 100% | 37% | 27% | 25% | 24% | 23% | 22% | 22% | 21% | 21% | 21% | 19% | 19% |
| | 25 | 100% | 44% | 34% | 32% | 30% | 30% | 30% | 29% | 29% | 28% | 29% | 26% | 25% |
| | 26 | 100% | 33% | 17% | 15% | 14% | 13% | 14% | 13% | 12% | 13% | 11% | 9% | 7% |
| | 27 | 100% | 39% | 32% | 30% | 29% | 29% | 28% | 28% | 26% | 26% | 26% | 24% | 23% |
| | 28 | 100% | 45% | 23% | 17% | 13% | 12% | 11% | 9% | 9% | 9% | 10% | 7% | 5% |
| | 29 | 100% | 46% | 42% | 27% | 26% | 24% | 23% | 23% | 22% | 22% | 21% | 19% | 18% |
| | 30 | 100% | 35% | 11% | 7% | 7% | 6% | 6% | 5% | 5% | 5% | 5% | 4% | 3% |
| Example 1 | 1 | 100% | 94% | 75% | 69% | 61% | 54% | 48% | 43% | 41% | 37% | 36% | 34% | 32% |
| | 2 | 100% | 64% | 52% | 49% | 45% | 41% | 37% | 36% | 30% | 34% | 33% | 23% | 22% |
| | 3 | 100% | 76% | 49% | 42% | 36% | 35% | 32% | 29% | 27% | 26% | 18% | 17% | 16% |
| | 4 | 100% | 72% | 39% | 37% | 32% | 31% | 27% | 25% | 25% | 24% | 21% | 14% | 10% |
| | 5 | 100% | 78% | 61% | 55% | 54% | 52% | 51% | 50% | 49% | 47% | 46% | 41% | 33% |
| | 6 | 100% | 79% | 56% | 45% | 42% | 39% | 37% | 36% | 34% | 30% | 29% | 25% | 21% |
| | 7 | 100% | 75% | 49% | 35% | 34% | 31% | 29% | 28% | 27% | 26% | 25% | 22% | 18% |
| | 8 | 100% | 73% | 55% | 45% | 39% | 35% | 33% | 31% | 28% | 28% | 27% | 20% | 15% |
| | 9 | 100% | 88% | 83% | 77% | 72% | 69% | 63% | 61% | 58% | 56% | 54% | 43% | 34% |
| | 10 | 100% | 84% | 70% | 59% | 54% | 50% | 49% | 47% | 45% | 44% | 42% | 32% | 22% |
| | 11 | 100% | 59% | 32% | 30% | 18% | 19% | 27% | 24% | 20% | 19% | 19% | 9% | 9% |
| | 12 | 100% | 51% | 40% | 35% | 35% | 29% | 26% | 26% | 31% | 27% | 26% | 22% | 20% |
| | 13 | 100% | 62% | 37% | 36% | 32% | 29% | 28% | 28% | 23% | 24% | 23% | 18% | 11% |
| | 14 | 100% | 44% | 28% | 25% | 22% | 21% | 19% | 18% | 19% | 19% | 12% | 8% | 5% |
| | 15 | 100% | 61% | 34% | 34% | 23% | 20% | 23% | 18% | 22% | 11% | 22% | 8% | 5% |
| | 16 | 100% | 79% | 43% | 36% | 34% | 33% | 30% | 30% | 29% | 28% | 28% | 19% | 17% |
| | 17 | 100% | 65% | 36% | 28% | 27% | 27% | 26% | 18% | 19% | 26% | 26% | 25% | 22% |
| | 18 | 100% | 52% | 36% | 33% | 30% | 26% | 23% | 21% | 21% | 19% | 19% | 18% | 16% |
| | 19 | 100% | 68% | 39% | 36% | 35% | 35% | 24% | 24% | 24% | 23% | 23% | 22% | 21% |
| | 20 | 100% | 67% | 47% | 29% | 36% | 32% | 32% | 25% | 25% | 24% | 11% | 11% | 7% |
| | 21 | 100% | 29% | 16% | 15% | 15% | 15% | 14% | 13% | 13% | 13% | 13% | 11% | 9% |
| | 22 | 100% | 41% | 42% | 21% | 38% | 25% | 30% | 26% | 33% | 26% | 30% | 10% | 13% |
| | 23 | 100% | 38% | 14% | 10% | 14% | 12% | 12% | 15% | 8% | 7% | 6% | 9% | 8% |
| | 24 | 100% | 35% | 31% | 30% | 29% | 28% | 28% | 27% | 26% | 26% | 25% | 22% | 13% |
| | 25 | 100% | 18% | 18% | 17% | 17% | 16% | 16% | 15% | 15% | 14% | 13% | 11% | 6% |
| | 26 | 100% | 46% | 37% | 35% | 25% | 24% | 38% | 34% | 23% | 32% | 33% | 20% | 11% |
| | 27 | 100% | 38% | 31% | 24% | 22% | 18% | 13% | 12% | 11% | 11% | 10% | 8% | 7% |
| | 28 | 100% | 66% | 52% | 41% | 37% | 33% | 29% | 29% | 28% | 27% | 24% | 15% | 8% |
| | 29 | 100% | 84% | 67% | 54% | 48% | 41% | 39% | 37% | 35% | 33% | 31% | 20% | 13% |
| | 30 | 100% | 80% | 52% | 41% | 37% | 33% | 30% | 28% | 27% | 25% | 24% | 16% | 11% |

The statistical analysis of the quantity of dry shampoo remaining (based on the weight measurements above) is provided in Table 13 below.

TABLE 13

Statistical analysis of quantity of dry shampoo remaining

| | | Quantity of dry shampoo remaining | | | | | | | | | | | |
|---|---|---|---|---|---|---|---|---|---|---|---|---|---|
| | Combing | 1 | 2 | 3 | 4 | 5 | 6 | 7 | 8 | 9 | 10 | 20 | 40 |
| Control | Mean | 50% | 30% | 24% | 22% | 21% | 20% | 19% | 18% | 19% | 18% | 14% | 11% |
| | Std | 16% | 11% | 10% | 9% | 9% | 9% | 9% | 9% | 9% | 8% | 9% | 8% |
| Example 1 | Mean | 62% | 44% | 38% | 35% | 32% | 30% | 28% | 27% | 26% | 25% | 19% | 15% |
| | Std | 19% | 17% | 15% | 13% | 13% | 12% | 11% | 11% | 11% | 11% | 9% | 8% |
| | Diff | −12% | −14% | −13% | −13% | −11% | −11% | −9% | −9% | −8% | −7% | −5% | −4% |
| | p-value | 0.005 | 0.000 | 0.000 | 0.000 | 0.000 | 0.000 | 0.000 | 0.001 | 0.002 | 0.003 | 0.024 | 0.041 |
| | significant | S | S | S | S | S | S | S | S | S | S | S | S |

For the hair tresses treated with the control formulation, 50% of the product was removed after the first shaking, as compared to the hair tresses treated with the formulation according to Example 1 above, wherein only 38% of the dry shampoo formulation was removed. The control formulation was faster to remove and after 10 combings, only 18% of the product remained on the hair, as compared to the hair tresses treated with the formulation according to Example 1, wherein 25% of the product remained after 10 combings. After 40 combings, 11% of the control formulation remained on the hair and 15% of the Example 1 formulation remained on the hair.

Figure 9:
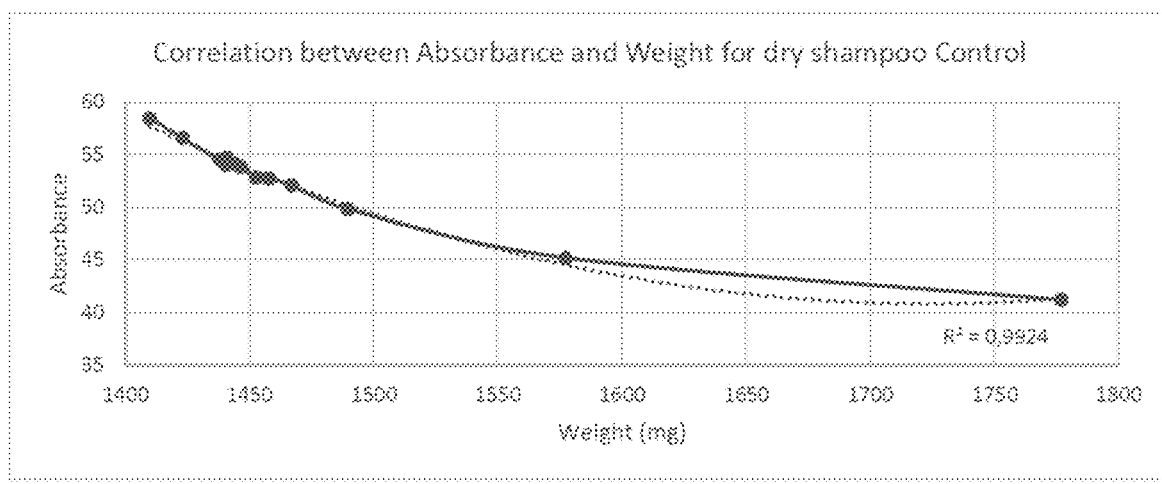
FIG. 9 is a plot showing the correlation between Absorbance and Weight for a control formulation after different numbers of combings.
Figure 10:
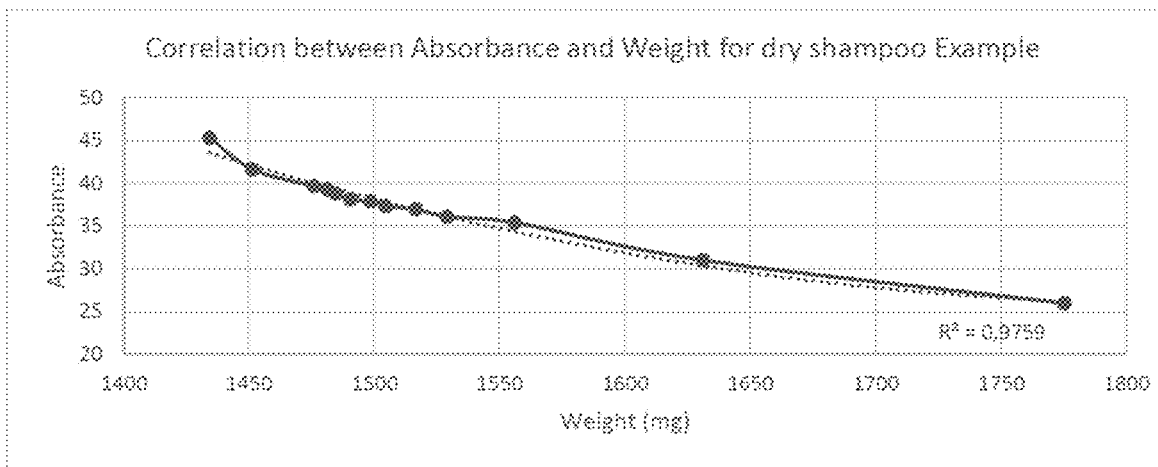
FIG. 10 is a plot showing the correlation between Absorbance and Weight for a formulation according to an embodiment of the dry shampoo compositions described herein after different numbers of combings.

The correlation between the visual estimation of the particles based on the luminance/absorbance of the particles and the weight of the dry shampoo particles was analyzed. FIG. 9 shows the correlation between Absorbance and Weight for the control formulation. FIG. 10 shows the correlation between Absorbance and Weight for the formulation according to Example 1 above. It was noted that the correlation factor between the luminance and the weight using a second degree polynomial function was very good with a correlation factor of 99.24% for the control dry shampoo and 97.59% for the Example 1 dry shampoo. This means that it is possible to estimate the weight of the remaining particles from the images based on the absorbance values, but the transfer function depends on the dry shampoo particles absorbance.

Figure 11:
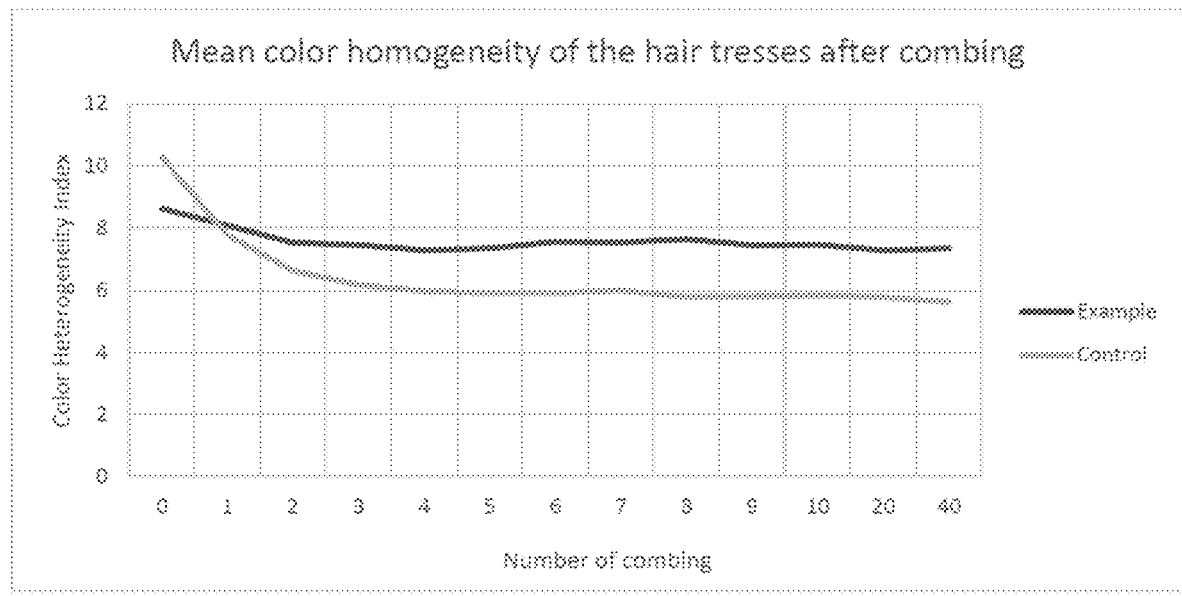
FIG. 11 is a graph showing the evolution of the mean heterogeneity parameter after each combing on hair tresses treated with a control dry shampoo formulation and for hair tresses treated with a dry shampoo formulation according to an embodiment of the present disclosure.

The color homogeneity of the dry shampoo formulations on the hair tresses was analyzed. The heterogeneity parameter (H76) was calculated on 3 areas of the hair tresses before application (naked hair tresses) of the dry shampoo, after application (0 combings) of the dry shampoo, and after each combing. FIG. 11 is a graph showing the evolution of the mean heterogeneity parameter after each combing on the 30 hair tresses for the control dry shampoo formulation and for the dry shampoo formulation according to Example 1 above. It was observed that the Control dry shampoo is less homogenous just after application. After the $2^{nd}$ combing, the color heterogeneity index for the two colored dry shampoo formulations is significantly different.

Table 14 below shows the evolution of the color heterogeneity index for the 2 dry shampoo formulations. It was observed that after the $4^{th}$ combing, the color homogeneity of the Control dry shampoo is stable whereas the color homogeneity of the dry shampoo formulation according to Example 1 above is stable after 2 combings and remains higher. After 40 combings, the color heterogeneity index difference between the Control formulation and the Example formulation is about 28%.

TABLE 14

Color Heterogeneity Index

| | | | Color Heterogeneity index | | | | | | | |
|---|---|---|---|---|---|---|---|---|---|---|
| | | Combing | Before | After | 1 | 2 | 3 | 4 | 5 | 6 |
| CONTROL | Mean | | 3.82 | 10.29 | 7.80 | 6.67 | 6.20 | 5.99 | 5.99 | 5.99 |
| | Std | | 0.97 | 1.15 | 1.29 | 0.69 | 0.56 | 0.57 | 0.58 | 0.48 |
| EXAMPLE | Mean | | 3.84 | 8.62 | 8.03 | 7.54 | 7.49 | 7.33 | 7.32 | 7.53 |
| | Std | | 0.96 | 0.92 | 0.85 | 0.68 | 0.69 | 0.73 | 0.75 | 0.85 |
| | Diff | | −0.47% | 16.29% | −2.94% | −13.15% | −20.68% | −22.42% | −22.29% | −25.66% |
| | p-value | | 0.472 | 0.000 | 0.216 | 0.000 | 0.000 | 0.000 | 0.000 | 0.000 |
| | significant | | N | S | N | S | S | S | S | S |

| | | | Color Heterogeneity index | | | | | |
|---|---|---|---|---|---|---|---|---|
| | | Combing | 7 | 8 | 9 | 10 | 20 | 40 |
| CONTROL | Mean | | 5.98 | 5.81 | 5.78 | 5.80 | 5.86 | 5.62 |
| | Std | | 0.56 | 0.49 | 0.56 | 0.48 | 0.52 | 0.45 |
| EXAMPLE | Mean | | 7.53 | 7.56 | 7.44 | 7.40 | 7.20 | 7.24 |
| | Std | | 0.84 | 0.96 | 0.96 | 1.02 | 1.06 | 0.64 |
| | Diff | | −25.84% | −30.09% | −28.70% | −27.65% | −22.99% | −28.68% |
| | p-value | | 0.000 | 0.000 | 0.000 | 0.000 | 0.000 | 0.000 |
| | significant | | S | S | S | S | S | S |

In conclusion, formulations prepared according to the present disclosure (i.e., including a hemisqualane) provide more long-lasting color effect than a dry shampoo composition which does not include a hemisqualane. Based on the weight, the conclusions on the evolution of the dry shampoo particles deposition are the same as the analysis of the absorbance analysis using image acquisition. The control dry shampoo was faster to remove from the hair tresses with 14% differences from the Example 1 dry shampoo after the first real combing. After 40 combings, 11% of the product remained for the control dry shampoo and 15% remained for the Example 1 dry shampoo. It was further noted that the hair tresses treated with the Example 1 dry shampoo were initially darker than the hair tresses treated with the control dry shampoo, and they remained darker at each measured combing throughout the 40 combings.

The analysis of the color homogeneity shows that the color homogeneity of the dry shampoo Example was more stable than the Control, whereas the dry shampoo Control color homogeneity was stable only after 4 combings, but its color was more homogenous (−28%) than the dry shampoo Example. Without intending to be limited by theory, this color homogeneity evolution can be explained in part by the presence of bigger dry shampoo particles after application of the dry shampoo Control as compared to the dry shampoo Example. After the loss of the bigger particles, the smaller particles are more homogenous in terms of color. This is also correlated with the weight evolution after each combing.

Many modifications and other embodiments of the disclosure will come to mind to one skilled in the art to which this disclosure pertains having the benefit of the teachings presented in the foregoing description; and it will be apparent to those skilled in the art that variations and modifications of the present disclosure can be made without departing from the scope or spirit of the disclosure. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A dry shampoo composition, comprising:
    a coloring agent comprising: a starch material and a colorant effective for imparting color to hair, the starch material and the colorant being blended and pulverized together to provide a uniform mixture of the starch material and the colorant;
    a color adhesion promoter that is effective as a film former and is present in an effective amount such that combing or brushing of the dry shampoo composition through the hair forms a coating of the coloring agent on the hair, the combination of the color adhesion promotor with the uniform mixture of the starch material and the colorant effectively improving adherence of the coloring agent to the hair after subsequent combings or brushings of the hair by improving resistance to removal of the coloring agent from the hair during the subsequent combings or brushings of the hair;
    a solvent; and
    optionally a propellant.

2. The dry shampoo composition of claim 1, wherein the color adhesion promoter comprises a $C_{13}$-$C_{15}$ alkane.

3. The dry shampoo composition of claim 1, wherein the color adhesion promoter comprises a long chain alkane.

4. The dry shampoo composition of claim 1, wherein the color adhesion promoter comprises hemisqualane.

5. The dry shampoo composition of claim 1, wherein the starch material comprises a rice starch.

6. The dry shampoo composition of claim 1, wherein the dry shampoo is substantially free of silicones.

7. The dry shampoo composition of claim 1, wherein the dry shampoo is substantially free of petroleum-based cationic surfactants.

8. The dry shampoo composition of claim 1, comprising:
    at least about 0.1 weight percent of the coloring agent, based on the total weight of the dry shampoo composition;
    at least about 0.1 weight percent of the color adhesion promoter, based on the total weight of the dry shampoo composition;
    at least about 0.1 weight percent of the solvent; and
    at least 50 weight percent of the propellant, based on the total weight of the dry shampoo composition.

9. The dry shampoo composition of claim 1, comprising:
    about 2 to about 10 weight percent of the coloring agent, based on the total weight of the dry shampoo composition;
    about 0.1 to about 10 weight percent of the color adhesion promoter, based on the total weight of the dry shampoo composition;
    about 2 to about 10 weight percent of the solvent; and
    about 70 to about 95 weight percent of the propellant, based on the total weight of the dry shampoo composition.

10. The dry shampoo composition of claim 1, further comprising a fragrance.

11. A method of cleansing and coloring hair, the method comprising applying a dry shampoo composition according to claim 1 to the hair.

12. The method of claim 11, comprising spraying the dry shampoo composition on the hair and combing or brushing the dry shampoo composition through the hair so as to form a film of the color adhesion promoter and the coloring agent on the hair.

* * * * *